US011510718B2

(12) United States Patent
Childers et al.

(10) Patent No.: US 11,510,718 B2
(45) Date of Patent: Nov. 29, 2022

(54) UNIVERSAL WIRE DRIVER

(71) Applicant: Stryker Corporation, Kalamazoo, MI (US)

(72) Inventors: Robert Warren Childers, Trinity, FL (US); Aman Deep Mathur, Rajasthan (IN); Chistopher Anthony Rossman, Comstock Park, MI (US)

(73) Assignee: Stryker Corporation, Kalamazoo, MI (US)

( * ) Notice: Subject to any disclaimer, the term of this patent is extended or adjusted under 35 U.S.C. 154(b) by 645 days.

(21) Appl. No.: 16/466,423

(22) PCT Filed: Nov. 21, 2017

(86) PCT No.: PCT/US2017/062754
§ 371 (c)(1),
(2) Date: Jun. 4, 2019

(87) PCT Pub. No.: WO2018/106445
PCT Pub. Date: Jun. 14, 2018

(65) Prior Publication Data
US 2019/0343568 A1 Nov. 14, 2019

Related U.S. Application Data

(60) Provisional application No. 62/430,614, filed on Dec. 6, 2016.

(51) Int. Cl.
*A61B 17/16* (2006.01)
*A61B 17/88* (2006.01)
*A61B 17/00* (2006.01)

(52) U.S. Cl.
CPC ...... *A61B 17/8861* (2013.01); *A61B 17/1697* (2013.01); *A61B 2017/00367* (2013.01); *A61B 2017/00477* (2013.01)

(58) Field of Classification Search
CPC ............ A61B 17/8861; A61B 17/1697; A61B 17/1753; A61B 17/162; A61B 17/846; A61B 17/1622; A61B 17/8872
See application file for complete search history.

(56) References Cited

U.S. PATENT DOCUMENTS

| 5,902,306 A | 5/1999 | Norman |
| 8,424,939 B2 | 4/2013 | Slack |

(Continued)

FOREIGN PATENT DOCUMENTS

| DE | 29916658 U1 | 12/1999 |
| EP | 1370180 B1 | 3/2008 |

(Continued)

OTHER PUBLICATIONS

International Search Report for Application No. PCT/US2017/062754 dated May 25, 2018, 18 pages.

(Continued)

*Primary Examiner* — Zade Coley
(74) *Attorney, Agent, or Firm* — Howard & Howard Attorneys PLLC

(57) ABSTRACT

A universal wire driver attachment comprises a driveshaft forming a lumen extending along a longitudinal axis. The driveshaft forms a plurality of channels extending perpendicularly from the longitudinal axis. The attachment further comprises a plurality of primary jaws movably disposed at least partially within the channels. The primary jaws comprise a plurality of wire gripping surfaces facing the longitudinal axis and configured to grip the surgical wire. The primary jaws cooperate with the channels such that the primary jaws are constrained from moving in an axial direction along the longitudinal axis. The primary jaws are capable of moving outward from the longitudinal axis when the surgical wire is inserted between the primary jaws, and the primary jaws are capable of being urged inward toward the longitudinal axis by the securing mechanism to increase a grip force on the surgical wire.

20 Claims, 21 Drawing Sheets

(56) References Cited

U.S. PATENT DOCUMENTS

2002/0151902 A1 10/2002 Riedel et al.
2010/0262127 A1* 10/2010 Schmied ............ A61B 17/1624
　　　　　　　　　　　　　　　　　　　　　　　　　606/1
2014/0276890 A1* 9/2014 Khosla ................ A61B 17/162
　　　　　　　　　　　　　　　　　　　　　　　　606/103

FOREIGN PATENT DOCUMENTS

FR　　　　2361186 A1　3/1978
WO　　2002076308 A2　10/2002
WO　　2016173254 A1　11/2016

OTHER PUBLICATIONS

English language abstract for DE29916658 not found. However, see machine assisted English language translation extracted from espacenet.com database on Jun. 4, 2019, 30 pages.
English language abstract and machine assisted English language translation for FR2361186 extracted from espacenet. com database on Jun. 4, 2019, 10 pages.
English language abstract and machine assisted English language translation for WO2016173254 extracted from espacenet. com database on Jun. 4, 2019, 15 pages.

* cited by examiner $D_1 \cong D_2$

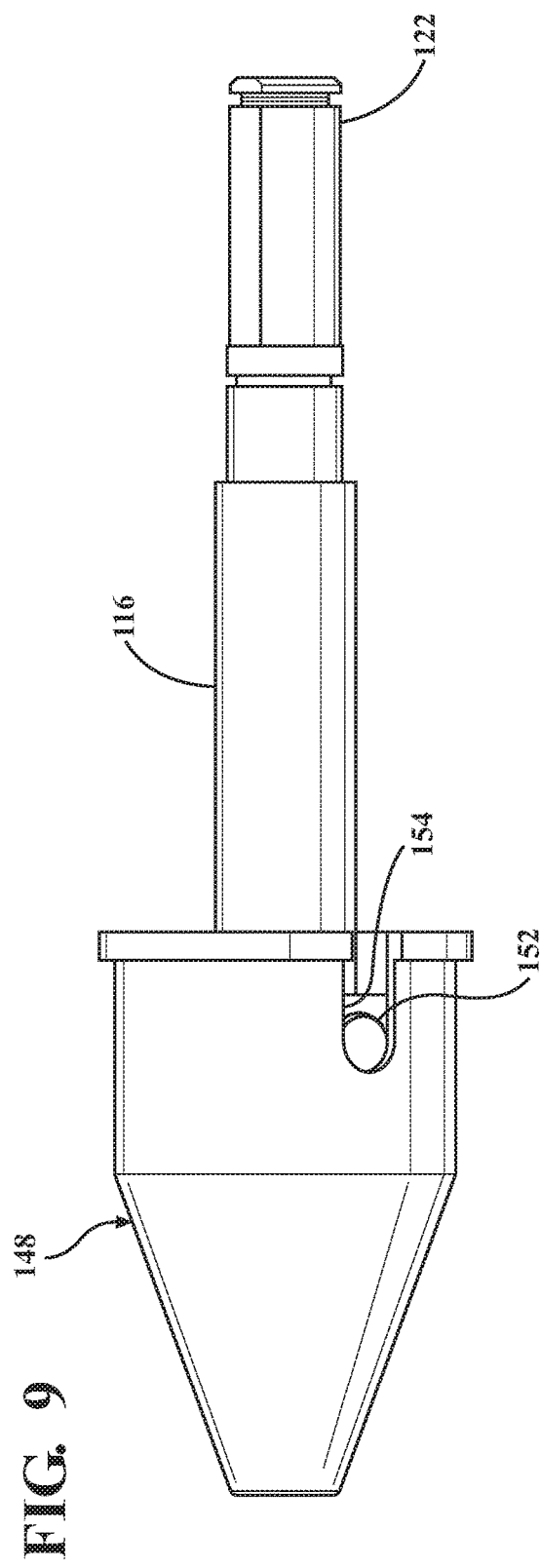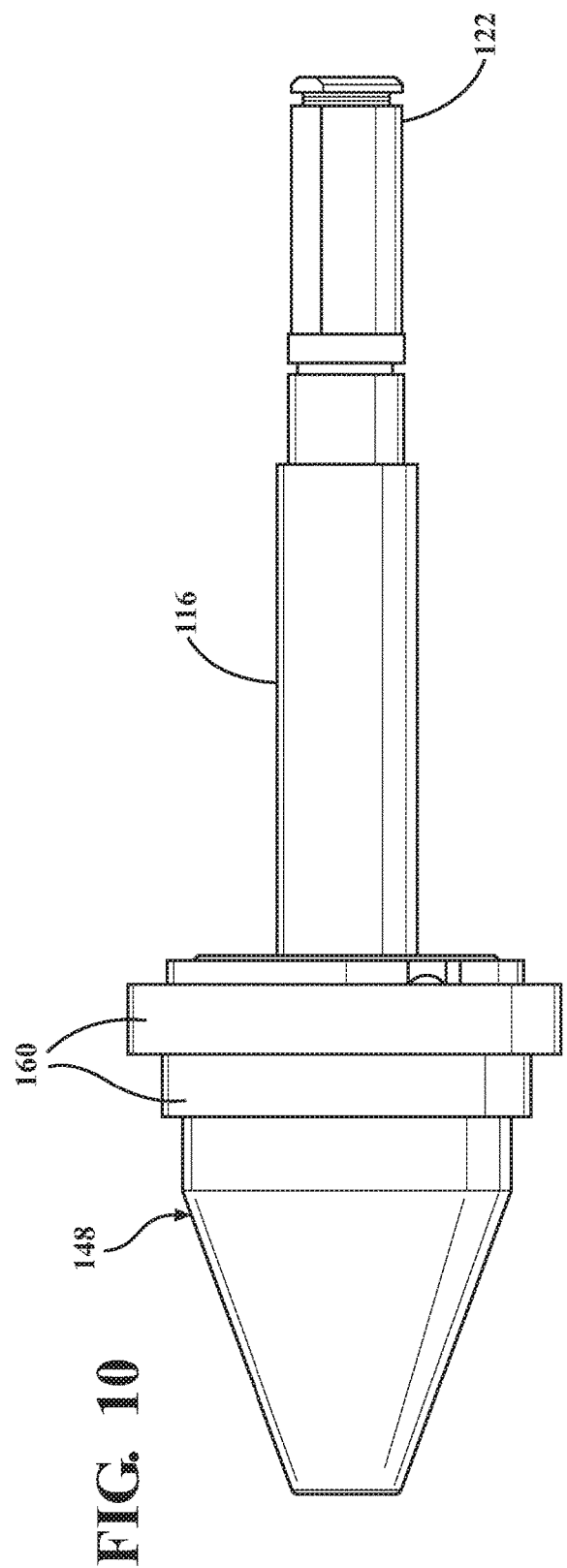

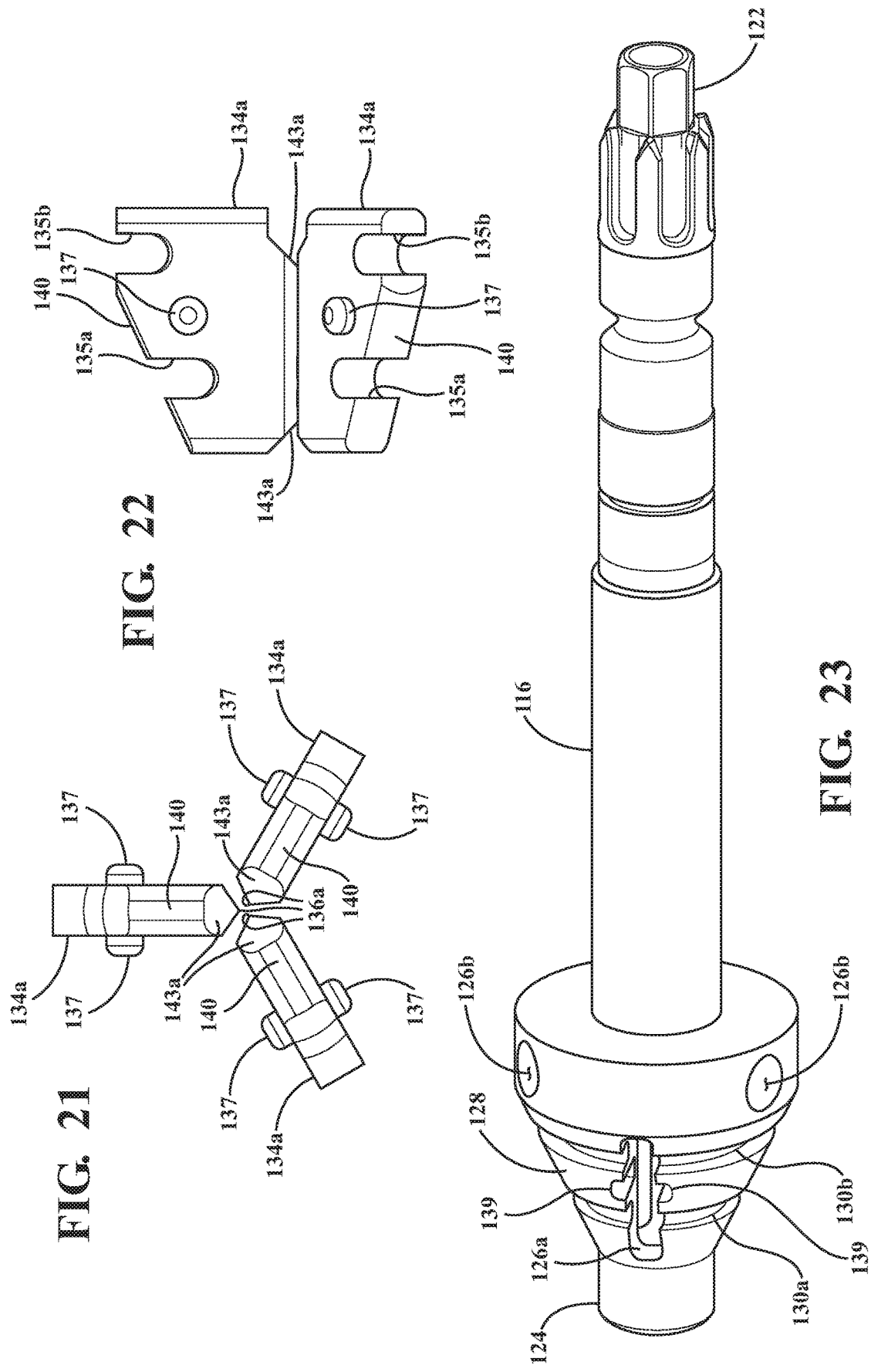

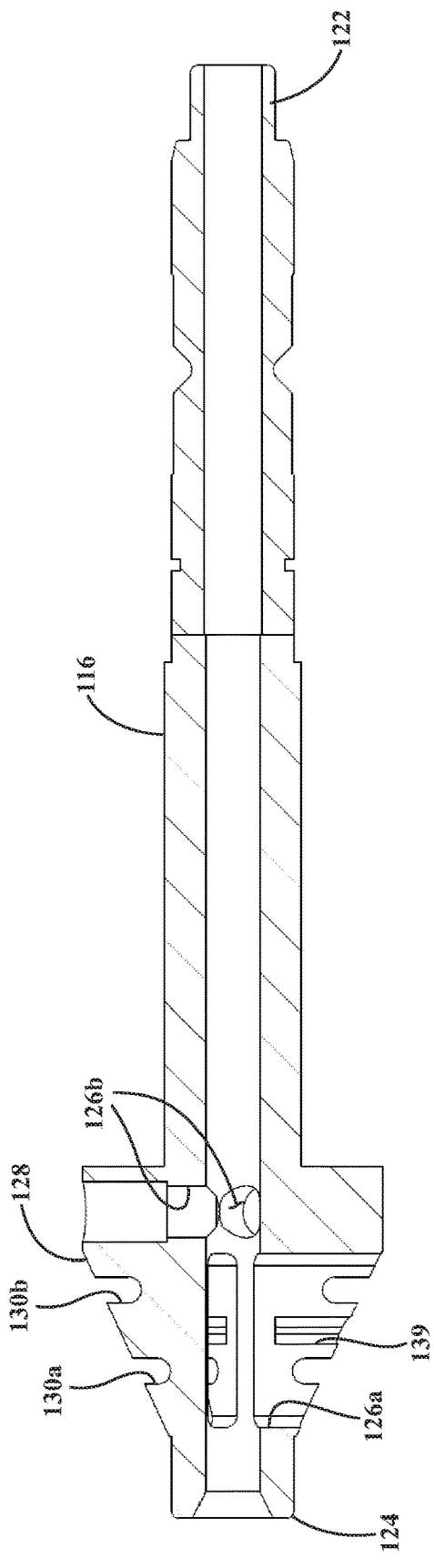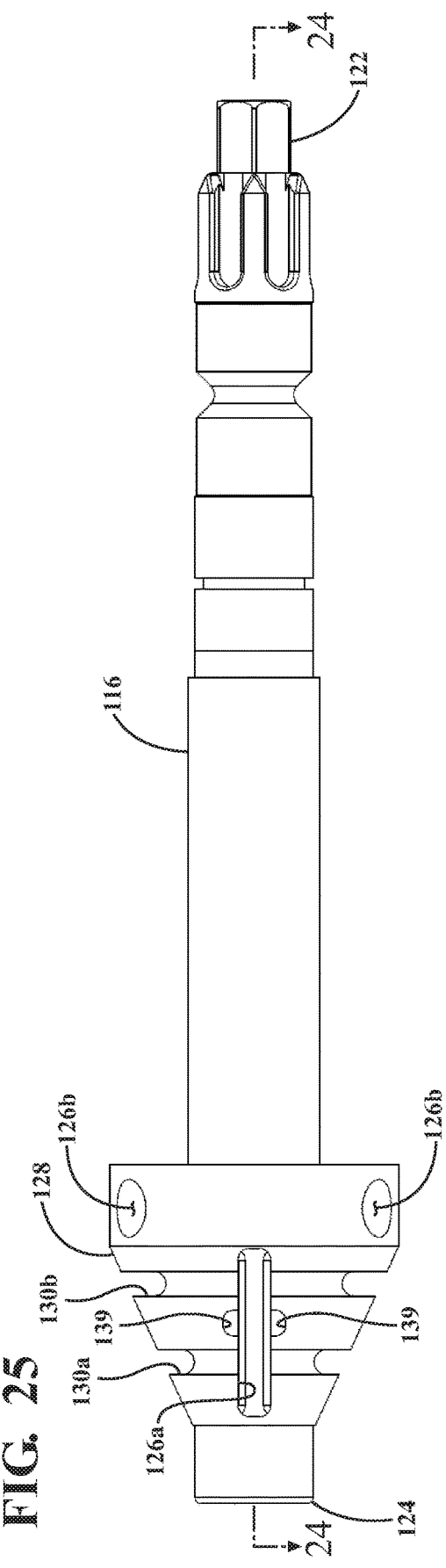

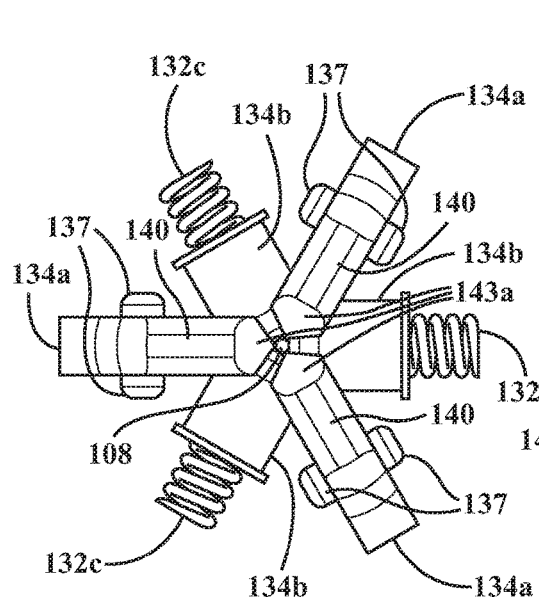
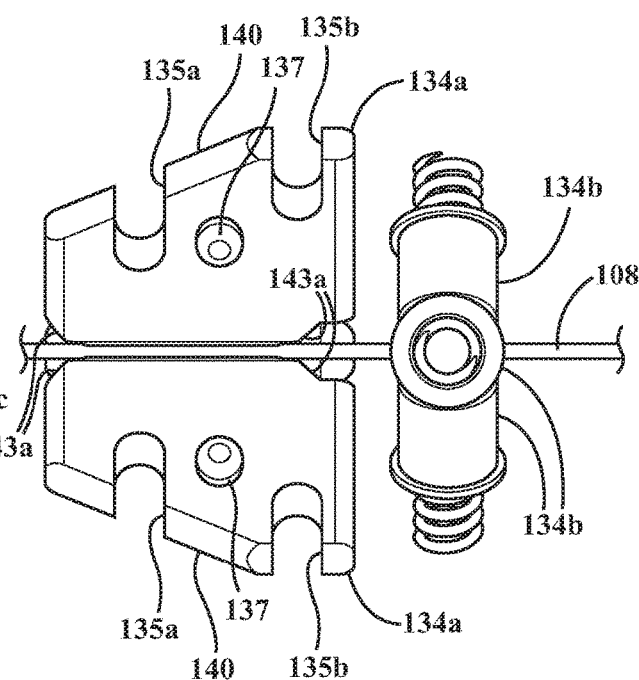
FIG. 26
FIG. 27
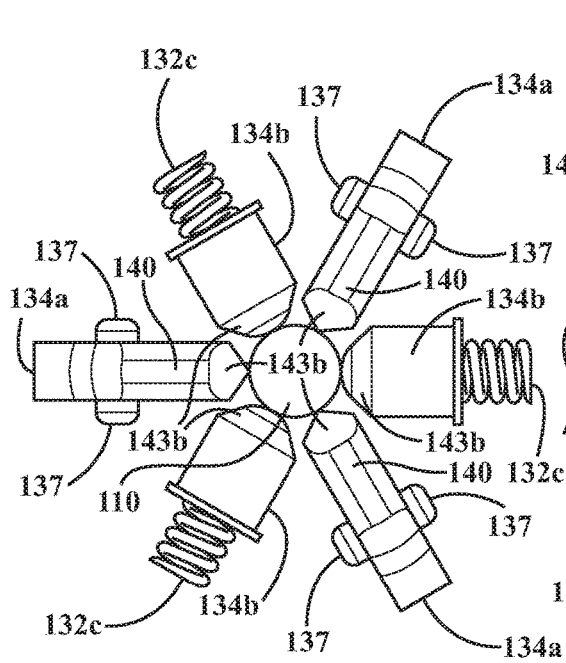
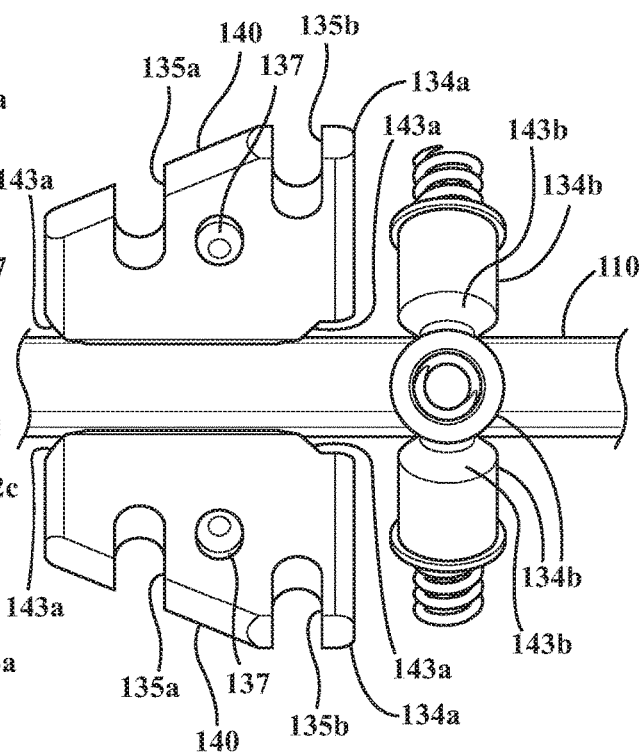
FIG. 28
FIG. 29

UNIVERSAL WIRE DRIVER

CROSS REFERENCE TO RELATED APPLICATION

This patent application claims priority to and the benefit of International Patent Application No. PCT/US2017/062754, filed Nov. 21, 2017, which claims priority to and the benefit of U.S. Provisional Patent Application No. 62/430,614, filed Dec. 6, 2016, the entire contents of which are hereby incorporated by reference.

TECHNICAL FIELD

The present disclosure relates to a universal wire coupler for coupling surgical wires having a range of diameters with a handheld surgical instrument

BACKGROUND OF THE DISCLOSURE

Wire drivers are used to place surgical wires and pins (collectively hereinafter "surgical wires") to secure bone during orthopedic procedures. Wire drivers may comprise a plurality of jaws movably displaced towards a closed position for gripping the surgical wires. The jaws may be movably displaced axially along a longitudinal axis such that the jaws protrude axially from the wire driver.

Other couplers may comprise a driveshaft terminating at a distal tip that comprises open channels and bulky washers or annular covers engaged with the distal tip to cover the channels for allowing a plurality of jaws to be displaced within associated channels towards the rotational axis. The coupler may further comprise a bearing and/or biasing device for engaging the washer with the distal tip of the driveshaft. The bearings may be bulky and obstruct a user's line of sight to the bone receiving the surgical wire and the tissue surrounding the bone.

It is desirable to provide a universal wire coupler for use with a wire driver to place surgical wires of various sizes in patients, facilitate with loading surgical wires into the wire driver before performing an orthopedic procedure, improve the user's line of sight to the bone receiving the surgical wire, and facilitate releasing surgical wires from the wire drivers after performing the orthopedic procedure.

BRIEF DESCRIPTION OF THE DRAWINGS

Referring now to the drawings, exemplary illustrations are shown in detail. Although the drawings represent examples, the drawings are not necessarily to scale and certain features may be exaggerated or be schematic in form to better illustrate and explain a particular aspect of an illustrative example. Any one or more of these aspects can be used alone or in combination within one another. Further, the exemplary illustrations described herein are not intended to be exhaustive or otherwise limiting or restricting to the precise form and configuration shown in the drawings and disclosed in the following detailed description. Exemplary illustrations are described in detail by referring to the drawings as follows:

FIG. 9 is a side view of the driveshaft of FIG. 8, illustrating the securing mechanism comprising a nose cone engaged with the driveshaft.

FIG. 10 is a side view of the driveshaft and nose cone of FIG. 9, illustrating a rotational bearing engaged with the nose cone.

FIG. 21 is an end view of the first plurality of jaws of FIG. 18, illustrating the jaws having guide pins for constraining axial movement of the jaws.

FIG. 22 is a side view of the first plurality of jaws of FIG. 21.

FIG. 23 is a perspective view of the driveshaft of FIG. 18, illustrating the driveshaft forming guide slots for receiving guide pins of the jaws therein to constrain axial movement of the jaws.

FIG. 24 is a cross-sectional view of the driveshaft of FIG. 23, illustrating the driveshaft forming one of the first plurality of channels and one of the second plurality of channels for movably displacing an associated one of the first and second jaws therein.

FIG. 25 is a side view of the driveshaft of FIG. 23, illustrating the driveshaft having guide slots capable of holding guide pins of the first jaws therein to constrain axial movement of the first jaws.

FIG. 26 is an end view of the first plurality of jaws and the second plurality of jaws of FIG. 18 capable of securing the first surgical wire to the handheld surgical instrument.

FIG. 27 is a side view of the first plurality of jaws and the second plurality of jaws of FIG. 26.

FIG. 28 is an end view of the first plurality of jaws and the second plurality of jaws of FIG. 18 capable of securing the second surgical wire to the handheld surgical instrument.

FIG. 29 is a side view of the first plurality of jaws and the second plurality of jaws of FIG. 28.

DETAILED DESCRIPTION

Figure 1:
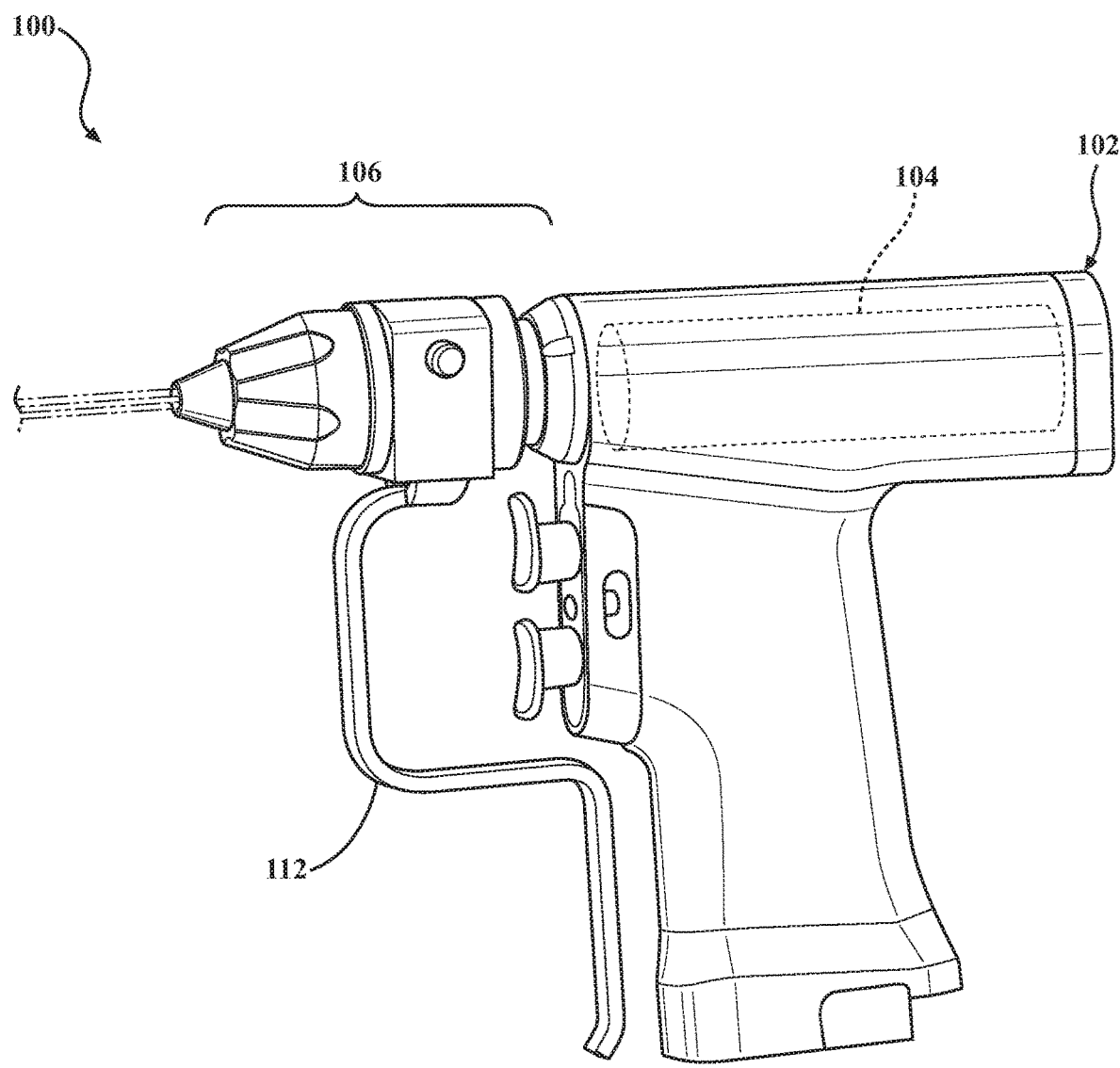
FIG. 1 is a perspective view of a handheld surgical instrument having a universal wire coupler for use with surgical wires having a range of diameters.

A universal wire driver attachment for coupling a surgical wire has one of a range of diameters with a handheld surgical instrument. The universal wire driver attachment comprises a driveshaft forming a lumen extending along a longitudinal axis. The driveshaft comprises a proximal region and a distal region forming a plurality of channels extending perpendicularly from the longitudinal axis. The wire driver attachment further comprises a plurality of primary jaws movably disposed at least partially within an associated one of the channels. The primary jaws comprise a plurality of wire gripping surfaces facing the longitudinal axis and configured to grip the surgical wire inserted therebetween. The primary jaws cooperate with the channels such that the primary jaws are constrained from moving in an axial direction along the longitudinal axis. The universal wire driver attachment further comprises an input device movably disposed between an actuated position and a non-actuated position. The universal wire driver attachment further comprises a securing mechanism engaged with the input device. The securing mechanism is movably disposed between a secured state when the input device is disposed in the actuated position and an unsecured state when the input device is disposed in the non-actuated position. The primary jaws are capable of moving outward from the longitudinal axis when the surgical wire is inserted between the primary jaws, and the primary jaws are capable of being urged inward toward the longitudinal axis by the securing mechanism to increase a grip force on the surgical wire when the securing mechanism is in the secured state.

A universal wire driver attachment for coupling a surgical wire has one of a range of diameters with a handheld surgical instrument. The universal wire driver attachment comprises a driveshaft forming a lumen extending along a longitudinal axis. The driveshaft comprises a proximal region and a distal region forming a first plurality of channels extending perpendicularly from the longitudinal axis and a second plurality of channels extending perpendicularly from the longitudinal axis. The universal wire driver attachment further comprises a first plurality of jaws movably disposed at least partially within an associated one of the first plurality of channels. The first plurality of jaws comprises a first plurality of wire gripping surfaces facing the longitudinal axis and configured to grip the surgical wire inserted therebetween. The universal wire driver attachment further comprises a second plurality of jaws movably disposed at least partially within an associated one of the second plurality of channels. The second plurality of jaws comprises a second plurality of wire gripping surfaces facing the longitudinal axis and configured to grip the surgical wire inserted therebetween. The universal wire driver attachment further comprises an input device movably disposed between an actuated position and a non-actuated position. The universal wire driver attachment further comprises a securing mechanism engaged with the input device. The securing mechanism is movably disposed between a secured state when the input device is disposed in the actuated position and an unsecured state when the input device is disposed in the non-actuated position. The universal wire driver attachment further comprises a biasing member engaged with at least one of the first plurality of jaws or the second plurality of jaws to urge the first plurality of jaws or the second plurality of jaws towards the lumen.

A wire driver for driving a surgical wire comprises a handpiece having a drive system. The wire driver further comprises a universal wire coupler capable of transmitting torque from the drive system to the surgical wire. The universal wire coupler comprises a driveshaft forming a lumen extending along a longitudinal axis. The driveshaft comprises a proximal region and a distal region forming a plurality of channels extending perpendicularly from the longitudinal axis. The universal wire coupler further comprises a plurality of primary jaws movably disposed at least partially within an associated one of the plurality of channels. The primary jaws comprise a plurality of wire gripping surfaces facing the longitudinal axis and configured to grip the surgical wire inserted therebetween. The primary jaws cooperate with the channels such that the primary jaws are constrained from moving in an axial direction along the longitudinal axis. The universal wire coupler further comprises an input device movably disposed between an actuated position and a non-actuated position. The universal wire coupler further comprises a securing mechanism engaged with the input device. The securing mechanism is movably disposed between a secured state when the input device is disposed in the actuated position and an unsecured state when the input device is disposed in the non-actuated position. The primary jaws are capable of moving outward from the longitudinal axis when the surgical wire is inserted between the primary jaws. The primary jaws are capable of being urged inward toward the longitudinal axis by the securing mechanism to increase a grip force on the surgical wire when the securing mechanism is in the secured state.

A universal wire driver attachment for coupling a surgical wire has one of a range of diameters with a handheld surgical instrument. The universal wire driver attachment comprises a driveshaft forming a lumen extending along a longitudinal axis. The driveshaft comprises a proximal region and a distal region forming a plurality of channels extending perpendicularly from the longitudinal axis. The universal wire driver attachment further comprises a plurality of primary jaws movably disposed at least partially within an associated one of the plurality of channels. The primary jaws comprise a plurality of wire gripping surfaces facing the longitudinal axis and configured to grip the surgical wire inserted therebetween. The universal wire driver attachment further comprises an input device movably disposed between an actuated position and a non-actuated position. The universal wire driver attachment further comprises a securing mechanism engaged with the input device. The securing mechanism is movably disposed between a secured state when the input device is disposed in the actuated position and an unsecured state when the input device is disposed in the non-actuated position. The primary jaws are capable of moving outward from the longitudinal axis when the surgical wire is inserted between the plurality of primary jaws, and the primary jaws are capable of being urged inward toward the longitudinal axis by the securing mechanism to increase a grip force on the surgical wire when the securing mechanism is in the secured state. One of the driveshaft or the primary jaws forms a plurality of guide slots disposed perpendicularly from the longitudinal axis, and the other of the driveshaft or the primary jaws comprises a plurality of pins movably disposed along an associated one of the guide slots such that the primary jaws are capable of moving outward from the longitudinal axis or inward towards the longitudinal axis while the primary jaws are constrained from moving in an axial direction along the longitudinal axis. The pins and the guide slots are capable of constraining the primary jaws from moving inward up to the longitudinal axis such that the primary jaws remain spaced outward from the longitudinal axis when the securing mechanism is in the secured state and the unsecured state.

The distal region of the driveshaft may comprise a plurality of channel surfaces surrounding an associated one of the plurality of channels to constrain the plurality of primary jaws from moving in the axial direction along the longitudinal axis.

The driveshaft may terminate at a distal end, and the plurality of primary jaws may be spaced apart from the distal end towards the proximal region of the driveshaft.

The distal region of the driveshaft may be free of a rotational bearing.

The driveshaft may comprise an outer surface facing the securing mechanism. Each one of the plurality of primary jaws may comprise a flange configured to engage the outer surface of the driveshaft and prevent the associated primary jaw from moving in an inward direction past the longitudinal axis of the driveshaft.

The plurality of wire gripping surfaces of the plurality of primary jaws may remain disposed in the lumen of the driveshaft when the securing mechanism is disposed in the secured state or the unsecured state.

The biasing member may be configured to urge the plurality of primary jaws inward toward the longitudinal axis to grip the surgical wire.

The biasing member may be a garter spring surrounding the plurality of primary jaws and holding the plurality of primary jaws within the plurality of channels of the driveshaft.

At least one of the plurality of primary jaws may comprise an inclined surface positioned at an angle relative to the longitudinal axis of the driveshaft. The inclined surface may form a notch configured to receive the biasing member.

The driveshaft may comprise an outer surface facing the securing mechanism and forming a plurality of grooves aligned with the notches of the primary jaws. The biasing member may be received within the notches and the grooves such that the notches and the grooves provide clearance for the securing mechanism.

At least one of the plurality of primary jaws may comprise an inclined surface positioned at an angle relative to the longitudinal axis of the driveshaft. The securing mechanism may be movably disposed along the longitudinal axis to engage the inclined surface and move the primary jaws inwardly toward the longitudinal axis.

The securing mechanism may comprise a wedge configured to urge the plurality of primary jaws towards the lumen of the driveshaft when the securing mechanism is transitioned from the unsecured state to the secured state.

The wedge may be operatively coupled to the input device, the wedge having an engagement surface positioned relative to the longitudinal axis at the angle corresponding with the plurality of inclined surfaces.

The driveshaft may comprise a proximal end and a distal end adjacent to the distal region. The wedge may be disposed between the plurality of primary jaws and the proximal end such that the wedge is movable forward toward the plurality of primary jaws for disposing the securing mechanism in the secured state and moving the plurality of primary jaws inward toward the longitudinal axis.

The securing mechanism may comprise a nose cone configured to urge the plurality of primary jaws towards the lumen of the driveshaft when the securing mechanism is transitioned from the unsecured state to the secured state.

The nose cone may be operatively coupled to the input device. The nose cone may comprise an engagement surface positioned relative to the longitudinal axis at the angle corresponding with the plurality of inclined surfaces.

The securing mechanism may further comprise a hood and a thruster. The hood may be linearly secured to the nose cone such that the hood and the nose cone are linearly movable in unison along the longitudinal axis. The hood may be capable of transmitting a thrust load to the nose cone for urging the plurality of primary jaws towards the lumen. The thruster may be capable of transmitting the thrust load from the input device to the hood when the securing mechanism is in the secured state and the input device is moved to the actuated position.

The hood may be rotatably coupled to the nose cone to permit the nose cone to freely rotate relative to the hood.

A bearing may be configured to transmit the thrust load from the hood to the nose cone while permitting the nose cone to rotate relative to the hood.

The driveshaft may comprise a distal end adjacent the distal region carrying the plurality of primary jaws. The nose cone may be disposed forward of the distal end such that the nose cone is movable rearward toward the plurality of primary jaws for disposing the securing mechanism in the secured state and moving the plurality of primary jaws inward toward the longitudinal axis.

The nose cone and the driveshaft may be movably disposable relative to one another along the longitudinal axis such that the nose cone is linearly movable along the longitudinal axis relative to the driveshaft when the securing mechanism is moved between the secured state and the unsecured state.

The nose cone and the driveshaft may be rotatably secured to one another such that the driveshaft is capable of transmitting torque to the nose cone to rotate the driveshaft and the nose cone in unison about the longitudinal axis.

One of the nose cone and the driveshaft may comprise a protrusion. The other of the nose cone and the driveshaft may comprise a nose cone slot extending parallel to the longitudinal axis and receiving the protrusion.

Referring to FIG. 1, a handheld surgical instrument 100 comprises a handpiece 102 having a drive system 104 and a universal wire coupler 106 capable of transmitting torque from the drive system 104 to surgical end effectors or implants, such as surgical wires or pins. The handheld surgical instrument 100 is illustrated in FIG. 1 as a modular instrument and the universal wire coupler 106 is a surgical wire driver attachment removably coupleable to the modular instrument for placing surgical wires having a range of diameters to secure bone fragments in a patient in a health care setting. Alternatively, the handheld surgical instrument 100 may not be a modular instrument but may rather comprise a dedicated wire driver, and the universal wire coupler may be an integral portion of the dedicated wire driver.

Figure 2:
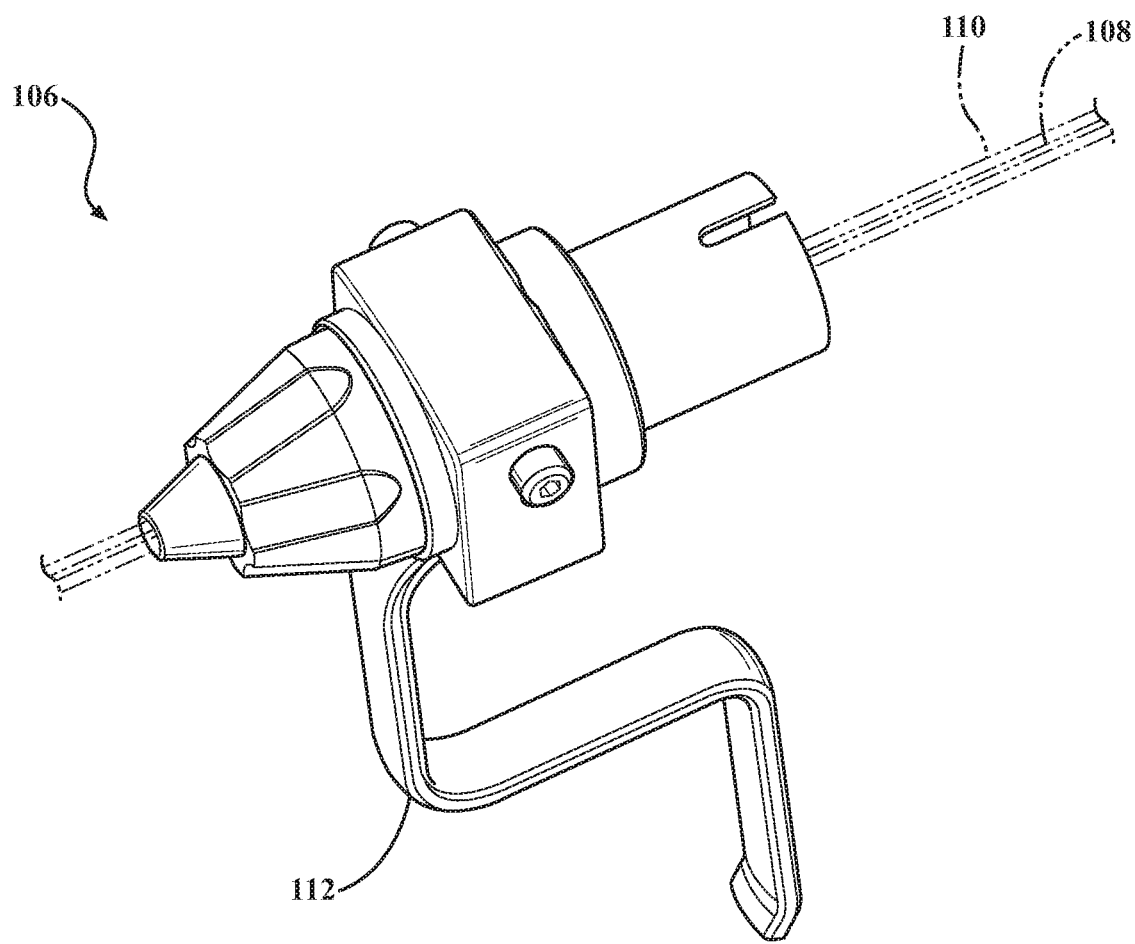
FIG. 2 is a perspective view of the universal wire coupler of FIG. 1.

Referring to FIG. 2, the universal wire coupler 106 may be capable of transmitting torque to a first surgical wire 108 having a first diameter equal to a minimum diameter threshold, a second surgical wire 110 having a second diameter that is equal to a maximum diameter threshold, and other surgical wires having diameters between the minimum and maximum diameter thresholds. As illustrated, the minimum diameter threshold may be 0.1 millimeters, and the maximum diameter threshold may be 5.0 millimeters. However, the universal wire coupler may be alternatively configured to transmit torque from the drive system to surgical wires having diameters less than 0.1 millimeters or more than 5.0 millimeters.

Figure 3:
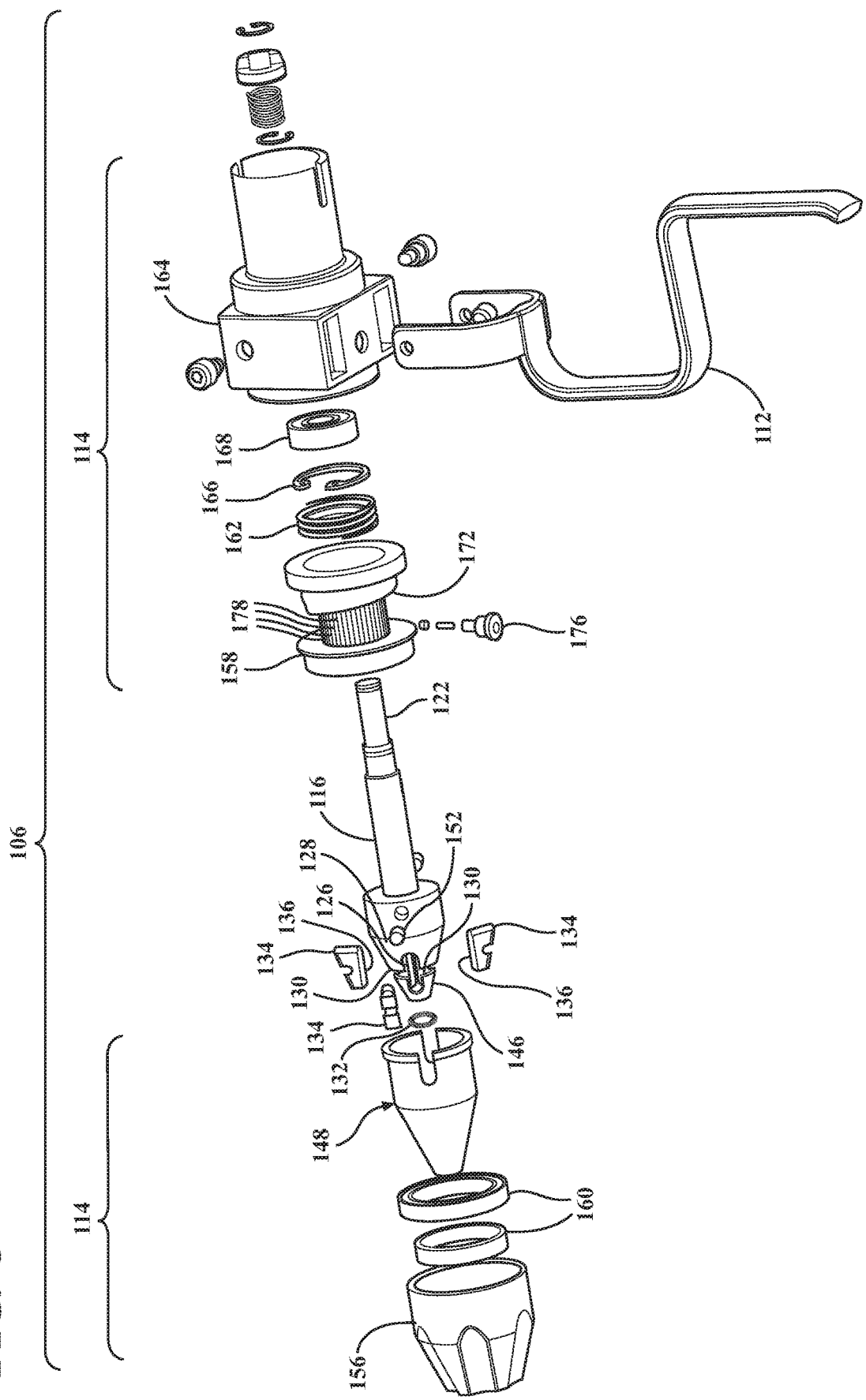
FIG. 3 is an exploded view of the universal wire coupler of FIG. 2, illustrating the universal wire coupler comprising an input mechanism, a securing mechanism, and a plurality of primary jaws movably disposed to grip surgical wire inserted between the primary jaws.

Referring to FIG. 3, the handheld surgical instrument 100 may comprise an input device 112 movably disposed between an actuated position and a non-actuated position. The handheld surgical instrument 100 may further comprise a securing mechanism 114 operably engaged with the input device 112. The securing mechanism 114 may be movably disposed between a secured state when the input device 112 is disposed in the actuated position and an unsecured state when the input device 112 is disposed in the non-actuated position.

Referring to FIG. 3, the universal wire coupler 106 may be a wire driver attachment removably coupleable to the handpiece 102. However, as described above, it is contemplated that the universal wire coupler can be an integral component of the handpiece. It is also contemplated that the handheld surgical instrument may comprise a modular system adaptable for use with a wire driver attachment and a plurality of other attachments and surgical end effectors that are removably coupleable to the handpiece.

Referring to FIGS. 4A through 5D, the universal wire coupler 106 may comprise a driveshaft 116 forming a lumen 118 positioned along a longitudinal axis 120 for receiving one or more surgical wires 108 (FIG. 4), 110 (FIG. 5). The driveshaft 116 may have a proximal region 122 and a distal region 124. The distal region 124 may terminate along the longitudinal axis 120 at a distal end 144 and include one or more channels 126 spaced from the distal end 144. The channels 126 may extend from the longitudinal axis 120 and be in communication with the lumen 118. As illustrated, each of the channels 126 are disposed at an angle α (FIGS. 5B and 5D) relative to the longitudinal axis 120, and α may be substantially perpendicular to the longitudinal axis 120. For example, α may range from 85 to 95, or approximately 90 degrees. It is contemplated that a may be above or below this range. As illustrated, a plurality of channel surfaces 138 may extend substantially perpendicular to the longitudinal axis 120 (or parallel to channel axis) to define an associated one of the channels 126. The driveshaft 116 further comprises an outer surface 128 facing the securing mechanism 114 as described in more detail below. The outer surface 128 may form one or more grooves 130 (FIG. 7) to accommodate a biasing member 132 (FIG. 8) as will also be described in more detail below.

The universal wire coupler 106 may further comprise a plurality of primary jaws 134. Each of the jaws 134 are movably disposed at least partially within an associated one of the channels 126. As illustrated, the universal wire coupler 106 may comprise three channels 126 and three primary jaws 134 uniformly disposed about the longitudinal axis 120. However, it is contemplated that the universal wire coupler 106 may alternatively comprise two, four, five, six, or any other suitable number of channels and primary jaws angularly spaced apart from one another by a uniform angle or a non-uniform angle.

The primary jaws 134 may each comprise a plurality of wire gripping surfaces 136 facing the longitudinal axis 120 and configured to grip the surgical wires 108, 110 inserted between the jaws 134. One or more of the wire gripping surfaces 136 may be configured to distribute a grip force along a portion of the surgical wires 108, 110 to reduce the risk of damaging the surgical wire 108, 110 such as by shaving the surgical wire 108, 110. One or more of the wire gripping surfaces 136 may comprise a double-beveled edge having a predetermined length parallel with the longitudinal axis 120 and configured to engage an associated predetermined length of the surgical wire 108, 110 to distribute the grip force along that length of the surgical wire 108, 110. However, the wire gripping surfaces may comprise different shapes and configurations other than the double-beveled edge described herein.

The driveshaft 116 is configured to constrain the primary jaws 134 from moving in an axial direction in both the secured and unsecured positions of the securing mechanism 114. The primary jaws 134, as illustrated, cooperate with the channels 126 such that the primary jaws 134 are constrained from moving in an axial direction relative to the longitudinal axis 120 in both the secured and unsecured position of the securing mechanism 114. More particularly, the primary jaws 134 may be axially constrained in the driveshaft 116 such that the jaws 134 cannot not move forward in the distal direction or backward in the proximal direction along the longitudinal axis 120 during actuation of the input device. As illustrated, the primary jaws 134 have opposing sides forming channel abutting surfaces 141 that abut the channel surfaces 138, which form the channels 126 and extend substantially perpendicular to the longitudinal axis 120 by the angle α. This permits the channel abutting surfaces 141 to constrain axial movement of the primary jaws 134. Alternatively, the primary jaws may cooperate with the channels in other suitable manners to constrain the primary jaws from moving in the axial direction.

It should be appreciated that the appropriate selection of α may reduce or prevent unintentional binding of the primary jaws 134 in the channels 126 after release of the input device 112. The driveshaft 116 and its channels as illustrated are configured to allow the primary jaws 134 to move perpendicularly outward to decrease the grip force on the surgical wire 108, 110 upon release of the input device 112. This reduces the grip force on the surgical wire when the securing device is in the unsecured position. The surgical wire 108, 110 is gripped between the jaws 134, which apply an equal and opposite force on each of the jaws outward from the longitudinal axis 120. One component of this force is a pushing force parallel to the axis of the channel 126, and another component of the force is a normal force, which is perpendicular to the outermost channel surfaces 138 and provides a frictional force based on the angle α. If all other conditions are equal, the frictional force will increase and the pushing force will decrease as the angle α is decreased or increased from 90 degrees. If α is selected such that the pushing force is greater than the frictional force, the surgical wire 108, 110 may displace the jaw sufficiently outward to permit the surgical wire 108, 110 to be removed from the jaws. If α is substantially 90 degrees, substantially all of the force of the surgical wire 108, 110 on the primary jaws 134 provides a pushing force on the primary jaws 134 and nearly none of that force provides a frictional force impeding movement of the primary jaws 134 within the channels 126.

The primary jaws 134 do not protrude axially from the distal end 144 of the driveshaft in part based on the jaws 134 being axially constrained. Because the primary jaws 134 do not protrude from the driveshaft 116, the primary jaws 134 remain spaced from the patient when a user uses the handheld surgical instrument 100 to perform the orthopedic procedure. In addition, the primary jaws 134 remain spaced apart from the gloves of a user who is loading surgical wire 108, 110 into the universal wire coupler 106 such that the user's gloves may not be inadvertently torn on the primary jaws 134.

The distal region 124 of the driveshaft 116 can be free of any rotational bearings or biasing members coupled directly to the distal end 144, such that the user's line of sight to bone receiving the surgical wire 108, 110 may not be obstructed by such bearings or biasing members. The universal wire coupler 106 can instead comprise a proximal bearing 160 (FIG. 3) coupled to the driveshaft 116 spaced from the user's line of sight. In other words, in certain configurations the universal wire coupler is free of any bearings, such as ball bearings, distal of the jaws.

The primary jaws 134 are not fixedly attached or connected to the input device 112 or the securing mechanism 114 for urging the primary jaws 134 inward toward the longitudinal axis 120 by a significant distance or outward from the longitudinal axis 120 during actuation. More particularly, the input device 112 is not attached or connected to the primary jaws 134, and hence, actuation of the input device 112 does not cause the primary jaws 134 to move outwardly from the longitudinal axis 120. Rather, the primary jaws 134 are configured to move outwardly away from the longitudinal axis 120 when the surgical wire 108, 110 is inserted between the primary jaws 134, the securing mechanism 114 is in the unsecured state, and the input device 112 is in the non-actuated position. Furthermore, while the securing mechanism 114 does engage the primary jaws 134 when the input device is in the actuated position, the securing mechanism 114 does not move the primary jaws a substantial distance because the jaws are already urged into contact with the surgical wire 108, 110 by the biasing member 132. In other words, the securing mechanism 114 and the primary jaws 134 are configured such that actuation of the input device 112 does not cause the primary jaws 134 to move more than 3, 2, or 1 mm inward toward the longitudinal axis 120 as the wire is elastically deformed by the gripping force.

The universal wire coupler 106 may include the biasing member 132 configured to urge the primary jaws 134 inward toward the lumen 118 and longitudinal axis 120 to a default closed state in which the jaws may or may not touch one another and to apply a pre-grip force to the surgical wire 108, 110 in the lumen 118. The primary jaws 134 are capable of moving outward from the longitudinal axis 120 when a user inserts or loads the surgical wire 108, 110 between the primary jaws 134 with an inserting force that is larger than the grip force applied by the biasing member 132. Primary jaws 134 preferably have a chamfered leading edge 143 adjacent to the gripping surface 136 to reduce the insertion force required to load surgical wire 108, 110 between the gripping surfaces of the jaws 134. The biasing member 132 urges the primary jaws 134 inward to apply the pre-grip force on the surgical wire 108, 110 and prevent the surgical wire 108, 110 from inadvertently falling to the floor. In other words, the biasing member 132 holds the wire gripping surfaces 136 of the primary jaws 134 within the lumen 118 of the driveshaft 116 to engage the surgical wire 108, 110 when the securing mechanism 114 is disposed in the unsecured state.

Figure 6:
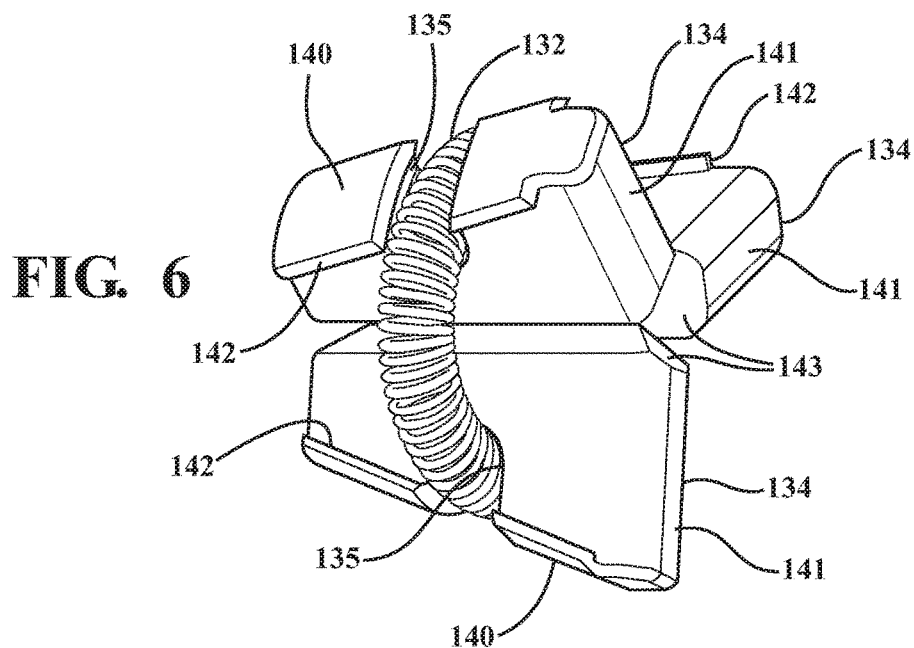
FIG. 6 is a perspective view of the primary jaws of FIG. 3, illustrating a biasing member surrounding the primary jaws.
Figure 7:
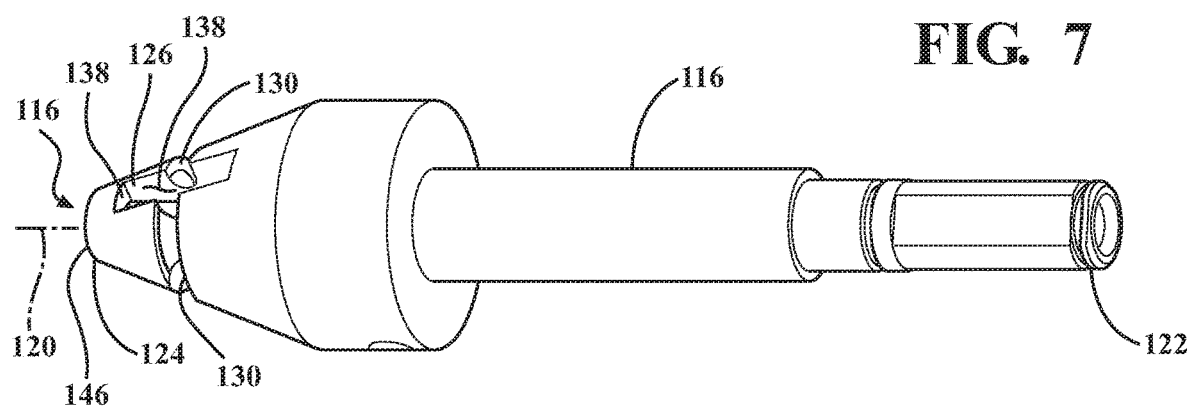
FIG. 7 is a perspective of the driveshaft of FIG. 3.
Figure 8:
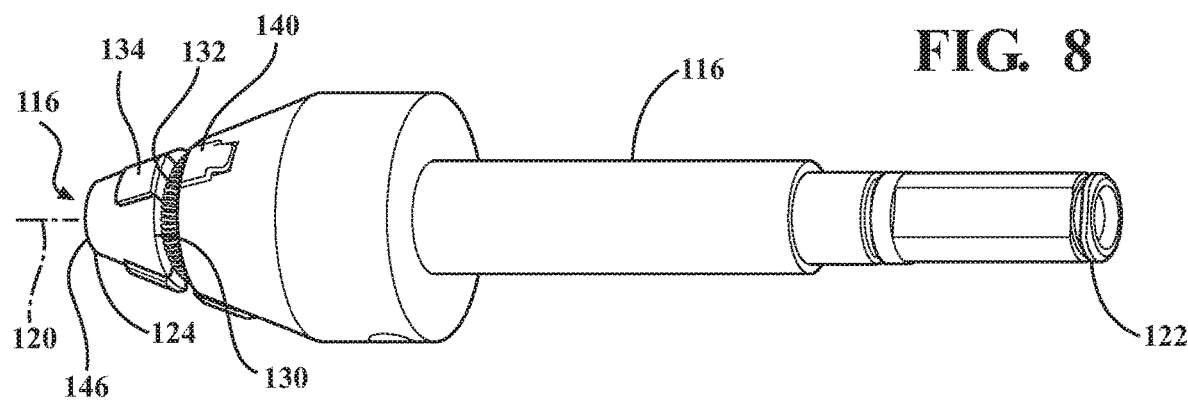
FIG. 8 is a perspective view of the driveshaft of FIG. 7, illustrating the primary jaws and biasing member engaged with the driveshaft.
Figure 11:
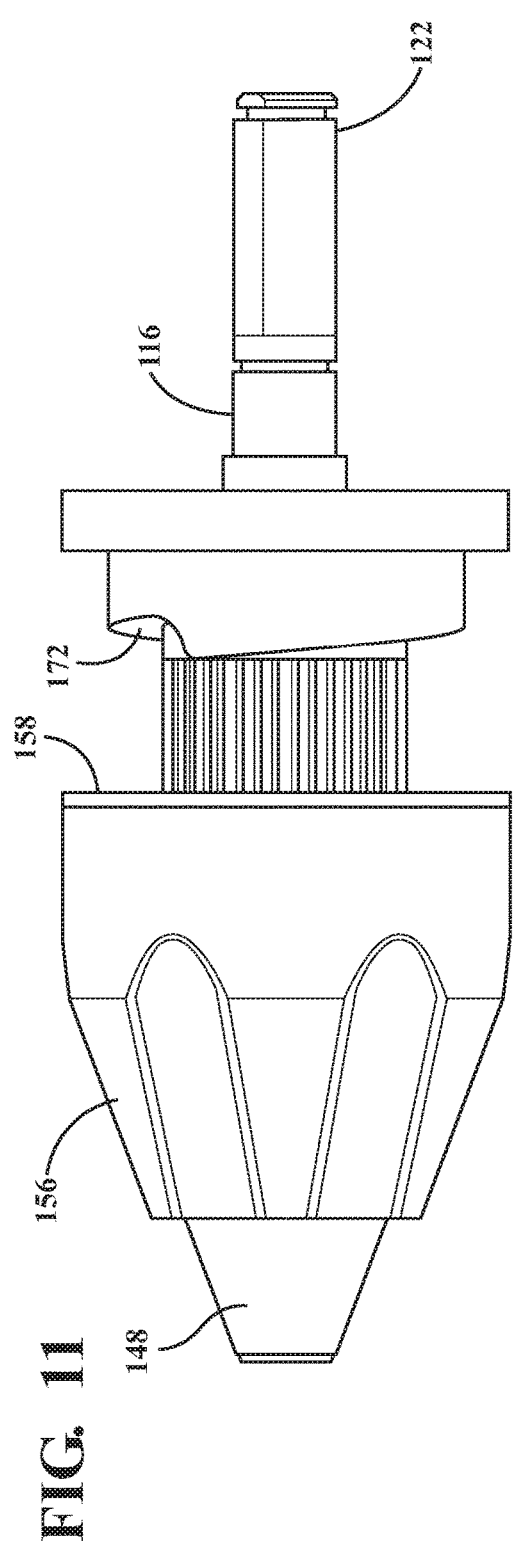
FIG. 11 is a side view of the driveshaft and nose cone of FIG. 10, illustrating the securing mechanism further comprising a hood engaged with the nose cone and a thruster engaged with the hood.
Figure 12:
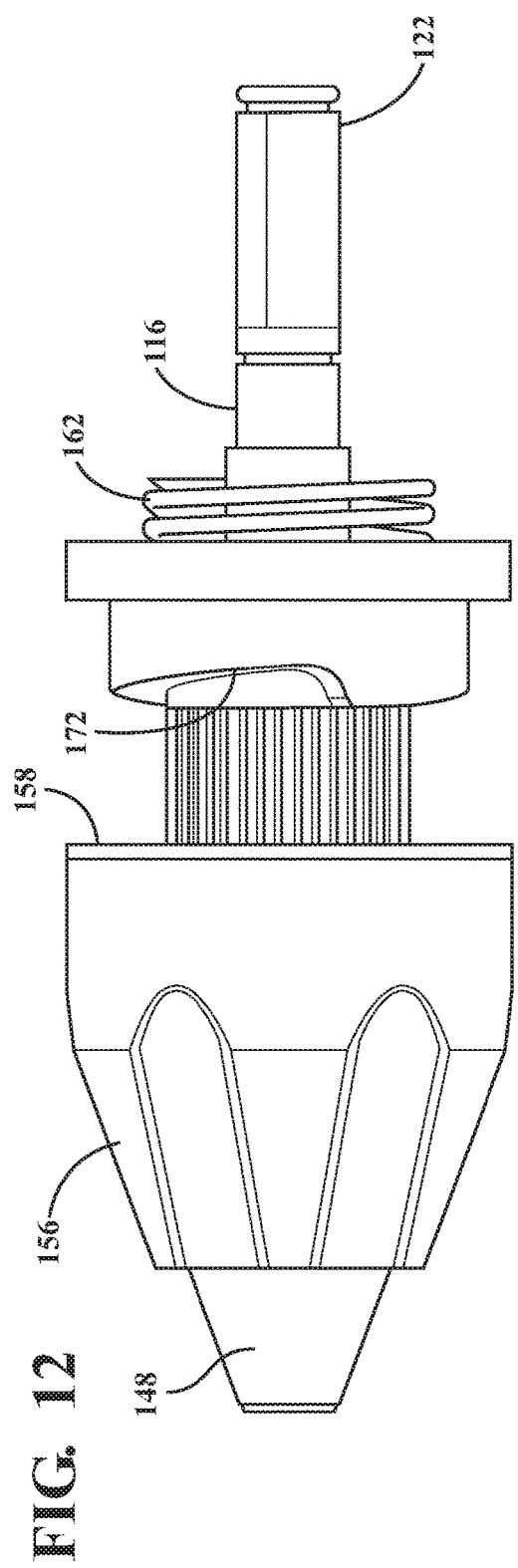
FIG. 12 is a side view of the driveshaft of FIG. 11, illustrating an urging mechanism engaged with the thruster to move the securing mechanism to the secured state.
Figure 13:
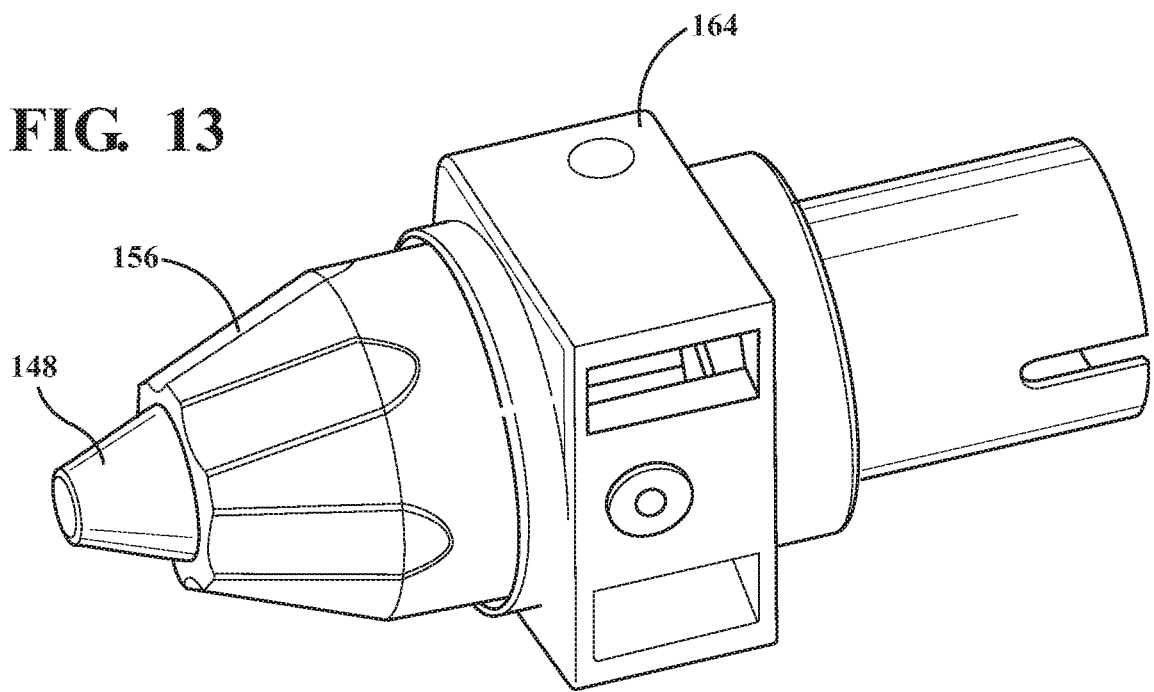
FIG. 13 is a perspective view of the driveshaft of FIG. 12, illustrating the securing mechanism further comprising a housing with the thruster movably displaced through the housing.
Figure 14:
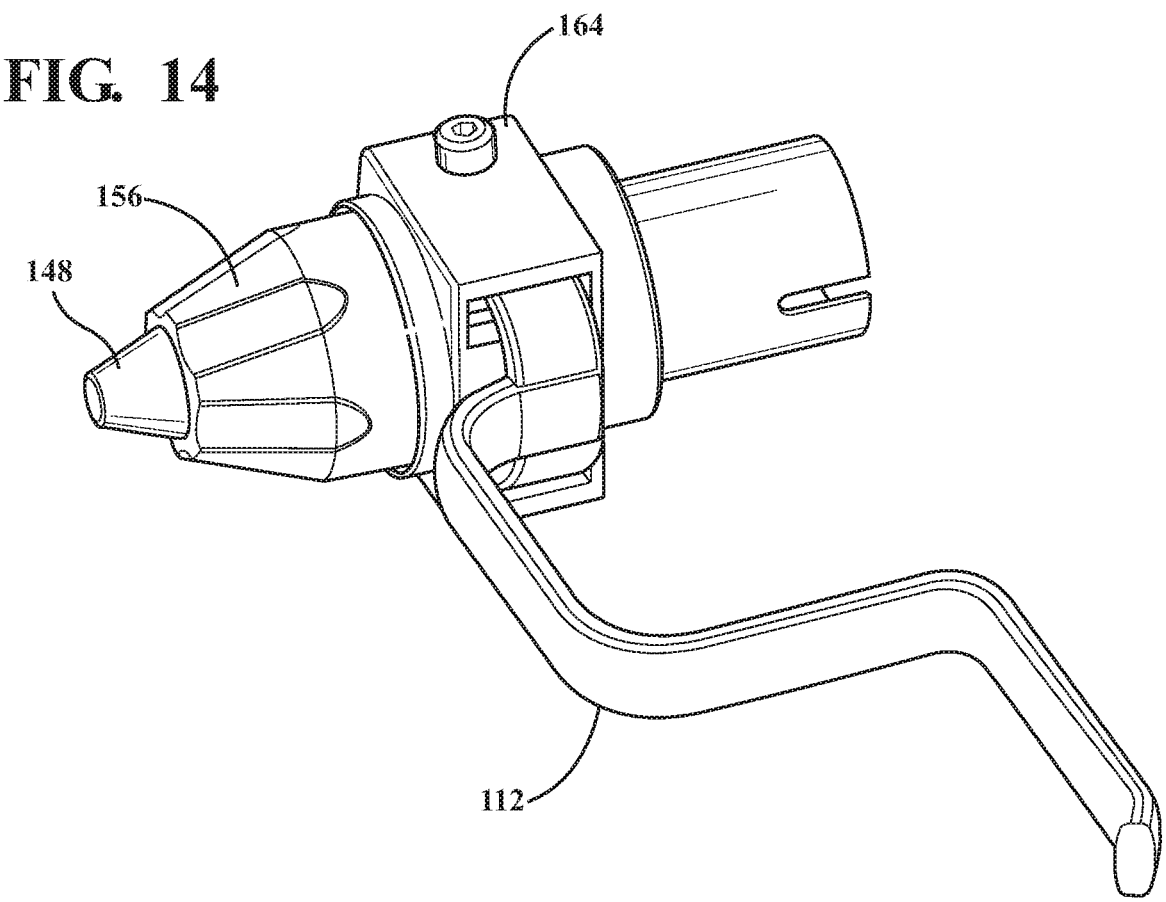
FIG. 14 is a bottom perspective view of the universal wire coupler, illustrating the universal wire coupler having an input device engaged with a housing and capable of moving a securing mechanism to a secured state.

Referring to FIGS. 6 and 8, the biasing member 132 may comprise a garter spring that surrounds the primary jaws 134 and holds the primary jaws 134 within the channels 126 of the driveshaft 116 such that the primary jaws 134 are at least partially disposed within the lumen (FIG. 7). At least one of the primary jaws 134 comprises an inclined surface 140 positioned at an angle relative to the longitudinal axis of the driveshaft 116. The inclined surface 140 of each primary jaw 134 forms a notch 135 aligned with associated grooves 130 formed in the outer surface 128 of the driveshaft 116. The biasing member 132 may be secured within the aligned notches 135 and grooves 130 to provide clearance for the securing mechanism 114 to move to the secured state for urging the primary jaws 134 inward towards the longitudinal axis 120.

The primary jaws 134 are further capable of being urged inward toward the longitudinal axis 120 by the securing mechanism 114 to increase the grip force on the surgical wires 108, 110 when the securing mechanism 114 is in the secured state. The securing mechanism 114 is movably disposed along the longitudinal axis 120 to engage the inclined surfaces 140 of the primary jaws 134 and move the primary jaws 134 inwardly toward the longitudinal axis 120 by a distance no greater than 1, 2, or 3 mm. Each of the primary jaws 134 may further comprise a flange 142 configured to engage the outer surface 128 of the driveshaft 116 (FIGS. 7 and 8) and prevent the associated primary jaw 134 from moving in an inward direction past the longitudinal axis 120 of the driveshaft 116. Alternately, flange 142 may prevent jaws 134 from touching when no wire is inserted to facilitate cleaning and sterilization.

Figure 4A:
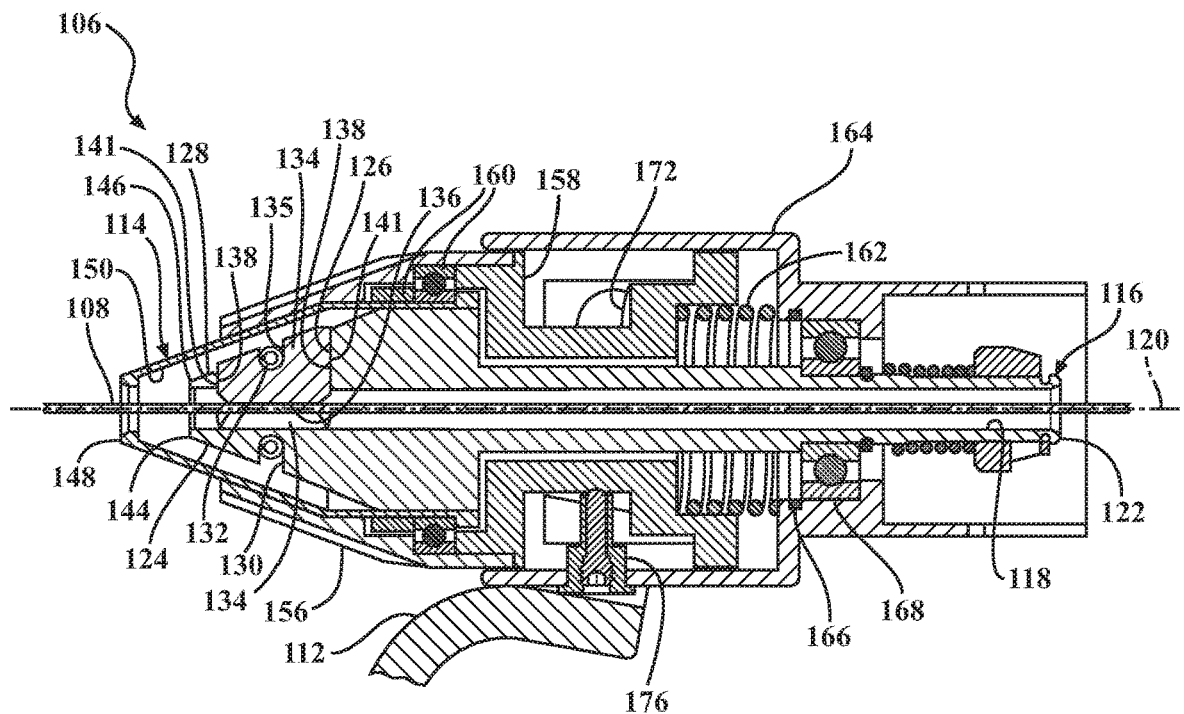
FIG. 4A is a cross-sectional view of the universal wire coupler of FIG. 3, illustrating the securing mechanism disposed in an unsecured state to permit the primary jaws to move outward from a longitudinal axis when a first surgical wire having a first diameter is inserted between the primary jaws.
Figure 4B:
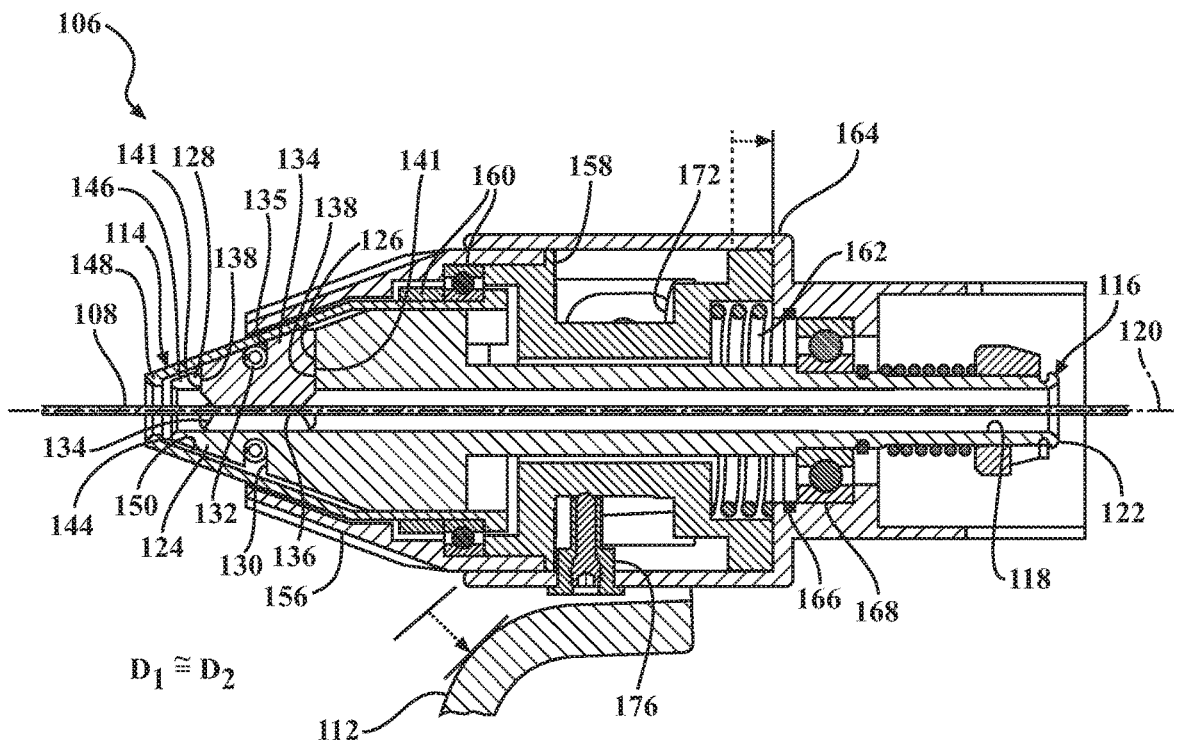
FIG. 4B is a cross-sectional view of the universal wire coupler of FIG. 4A, illustrating the securing mechanism movably disposed in a proximal direction towards a secured state for urging the primary jaws inward towards the longitudinal axis to increase the grip force on the first surgical wire.
Figure 5A:
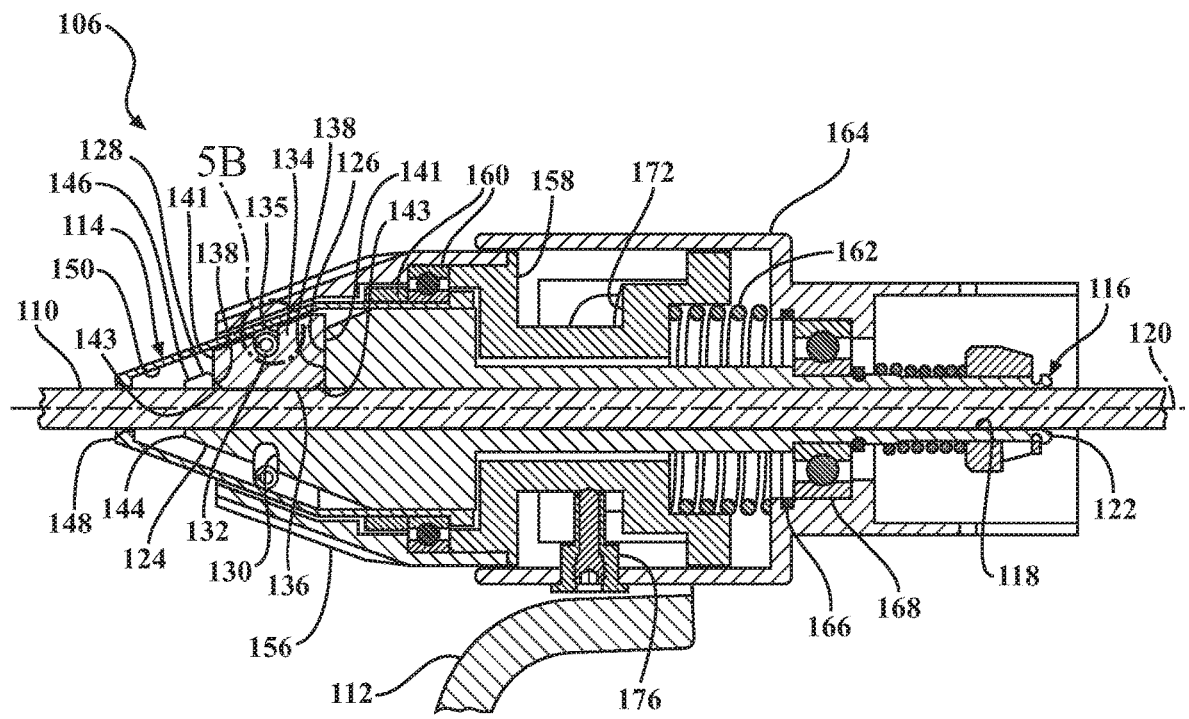
FIG. 5A is a cross-sectional view of the universal wire coupler of FIG. 3, illustrating the securing mechanism disposed in an unsecured state to permit the primary jaws to move outward from a longitudinal axis when a second surgical wire having a second diameter is inserted between the primary jaws.
Figure 5B:
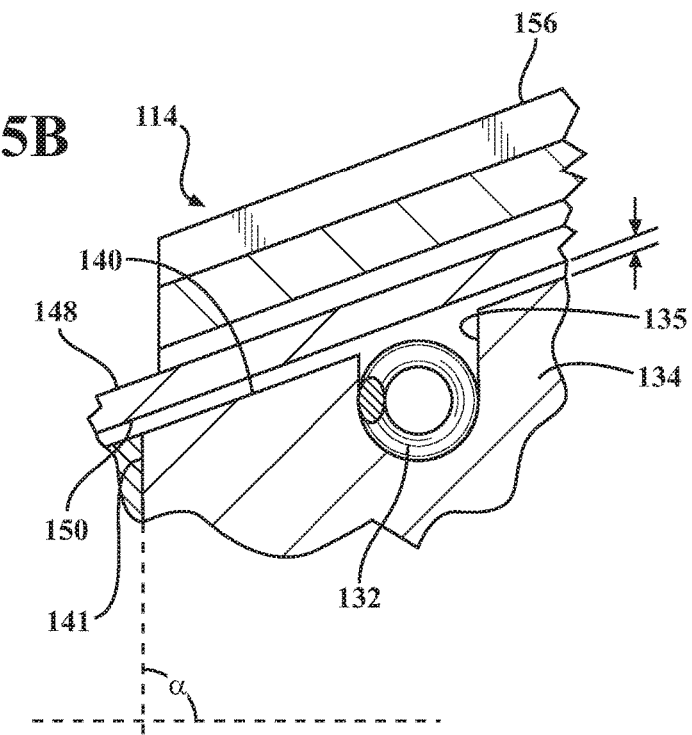
FIG. 5B is an enlarged view of the universal wire coupler of FIG. 5A, illustrating the securing mechanism in the unsecured state being spaced apart from the primary jaws.
Figure 5C:
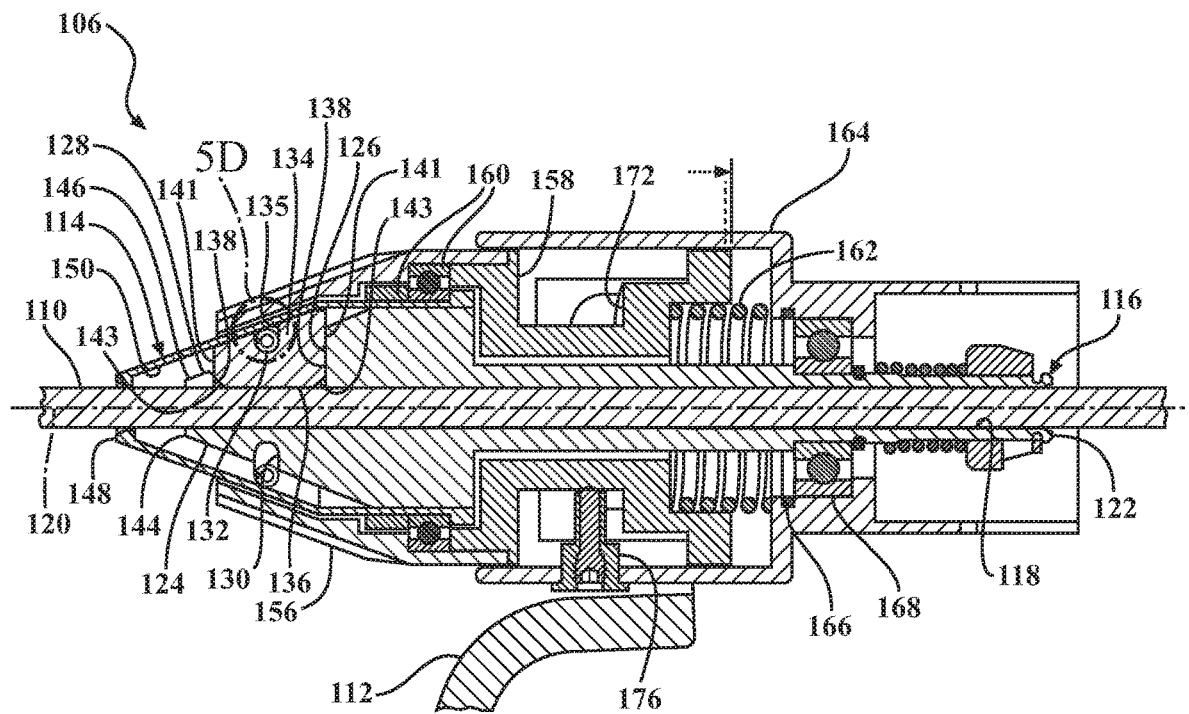
FIG. 5C is a cross-sectional view of the universal wire coupler of FIG. 5A, illustrating the securing mechanism movably disposed in a proximal direction towards a secured state for urging the primary jaws inward towards the longitudinal axis to increase the grip force on the second surgical wire.
Figure 5D:
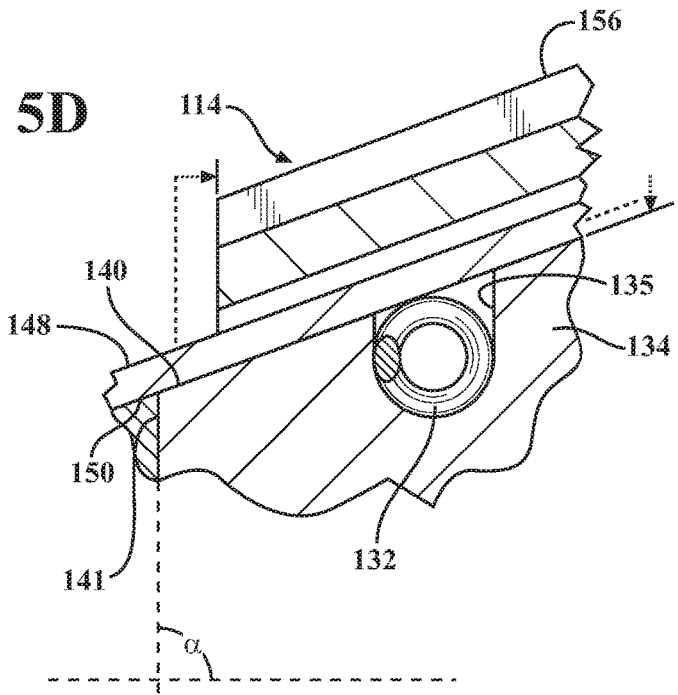
FIG. 5D is an enlarged view of the universal wire coupler of FIG. 5C, illustrating the securing mechanism in the secured state abutting against the primary jaws.

Referring to FIGS. 4A through 5D, the securing mechanism 114 comprises a nose cone 148 disposed forward of the distal end 144. FIG. 4A illustrates the securing mechanism 114 disposed in the unsecured state for inserting the first surgical wire 108 between the jaws 134, and FIG. 4B illustrates the securing mechanism 114 disposed in the secured state for increasing the grip force of the jaws on the first surgical wire 108. FIGS. 5A and 5B illustrate the securing mechanism 114 of FIG. 4A disposed in an unsecured state for inserting the second surgical wire 110 between the jaws 134. FIGS. 5C and 5D illustrate the securing mechanism 114 of FIG. 4B disposed in a secured state for increasing the grip force of the jaws 134 on the second surgical wire 110.

The nose cone 148 comprises an engagement surface 150 positioned relative to the longitudinal axis 120 at the same angle corresponding with the inclined surfaces 140 of the primary jaws 134. The nose cone 148 is movable in a distal direction relative to the primary jaws 134 when the input device is disposed in a non-actuated position and the securing mechanism 114 is disposed in the unsecured state. When the securing mechanism 114 is in the unsecured state, the engagement surface 150 of the nose cone 148 is disengaged from the primary jaws 134 and spaced from the primary jaws 134, such that the surgical wire 108 (FIG. 4A), 110 (FIGS. 5A and 5B) between the jaws 134 may urge the primary jaws 134 outward from the longitudinal axis 120. FIG. 4A illustrates the securing mechanism 114 in the unsecured state. The biasing member 132 continues to urge the primary jaws 134 toward the longitudinal axis 120 and against the surgical wire 108, 110, such that the primary jaws 134 engage the surgical wire 108, 110 with at least a minimum grip force when the secured mechanism is in either one of the secured state or the unsecured state. The nose cone 148 is movable in a proximal direction rearward toward the primary jaws 134 for disposing the securing mechanism 114 in the secured state and engaging the primary jaws 134 to increase the grip force on the surgical wire 108 (FIG. 4B), 110 (FIGS. 5C and 5D).

As described in detail below, the securing mechanism may alternatively be configured to move in a distal direction forward toward the primary jaws for disposing the securing mechanism in the secured state and a proximal direction away from the proximal jaws for disposing the securing mechanism in the unsecured state. Furthermore, it should be appreciated that other suitable securing mechanisms may be used to engage the jaws and cause the jaws to be in the secured state or the unsecured state.

Referring to FIG. 9, the nose cone 148 and the driveshaft 116 are movably disposable relative to one another along the longitudinal axis 120 such that the nose cone 148 is linearly displaceable along the longitudinal axis 120 relative to the driveshaft 116 when the securing mechanism 114 is moved between the secured state and the unsecured state. Furthermore, the nose cone 148 and the driveshaft 116 are rotatably secured to one another such that the driveshaft 116 is capable of transmitting torque to the nose cone 148 to rotate the driveshaft 116 and the nose cone 148 in unison about the longitudinal axis. In particular, the nose cone 148, the driveshaft 116, and the primary jaws 134 in the driveshaft rotate in unison when the nose cone 148 engages the primary jaws 134 to increase grip force on the surgical wire 108, 110. The driveshaft 116 may comprise a protrusion 152 and the nose cone 148 comprises a nose cone slot 154 extending parallel to the longitudinal axis 120 and receiving the protrusion 152. Alternatively, the driveshaft may form the slot parallel with the longitudinal axis, and the nose cone may comprise the protrusion received within the slot. It is contemplated that the driveshaft and the nose cone can have any suitable coupling which results in a capability of movably displacing the nose cone and driveshaft relative to one another and transmitting torque from the driveshaft to the nose cone.

Referring again to FIGS. 3 through 5D, the securing mechanism 114 may further comprise a hood 156 linearly secured to the nose cone 148 such that the hood 156 and the nose cone 148 are linearly movable in unison along the longitudinal axis 120 when the securing mechanism is moved between the unsecured and secured states. The hood 156 may be capable of transmitting a thrust load to the nose cone 148 to urge the primary jaws 134 towards the lumen 118 when the securing mechanism 114 is in the secured state.

Referring to FIGS. 3 through 5A, 5C, and 11, the securing mechanism 114 may further comprise a thruster 158 capable of transmitting the thrust load from the input device 112 to the hood 156 when the securing mechanism 114 is in the secured state and the input device 112 is moved to the actuated position. The hood 156 is rotatably coupled to the nose cone 148 to permit the nose cone 148 to freely rotate relative to the hood 156. The securing mechanism 114 may comprise at least one bearing 160 (FIGS. 3 through 5 and 10) configured to transmit the thrust load from the hood 156 to the nose cone 148 when the securing mechanism 114 is in the secured state, while permitting the nose cone 148 to rotate relative to the hood 156. As described above, this bearing 160 is proximal to the primary jaws.

Referring to FIGS. 3 through 5A, 5C, and 12, the securing mechanism 114 may further comprise an urging mechanism 162 for biasing the securing mechanism towards the unsecured state and reducing the grip force on the surgical wire 108, 110. The urging mechanism 162 may be a compression spring engaging the thruster 158 for moving the thruster 158, hood 156, and nose cone 148 axially in a distal direction away from the primary jaws 134. It is contemplated that the securing mechanism can have other suitable urging mechanisms or no urging mechanisms. The input device 112 may push the securing mechanism forward toward its unsecured state by moving the thruster 158, hood 156, and nose cone 148 axially in a distal direction away from the primary jaws 134 when the input device 112 is moved to the non-actuated position.

Referring to FIGS. 3 through 5A, 5C, and 13, the securing mechanism 114 may further comprise a housing 164 receiving at least a portion of the driveshaft 116 and thruster 158. A ball bearing 168 (FIG. 3) capable of withstanding both radial and thrust loads may be secured into the housing 164 and an internal snap ring 166 or other suitable fastener holds the ball bearing 168 in the housing 164. The input device 112 is engaged with the housing 164 and movable to the actuated position for applying an axial force to the thruster 158 (FIGS. 4B and 5C) and moving the securing mechanism 114 to the secured state from the unsecured state. Alternatively, the input device may be placed external to the housing and apply an axial force to the thruster through slots formed in each side of the housing.

Figure 15:
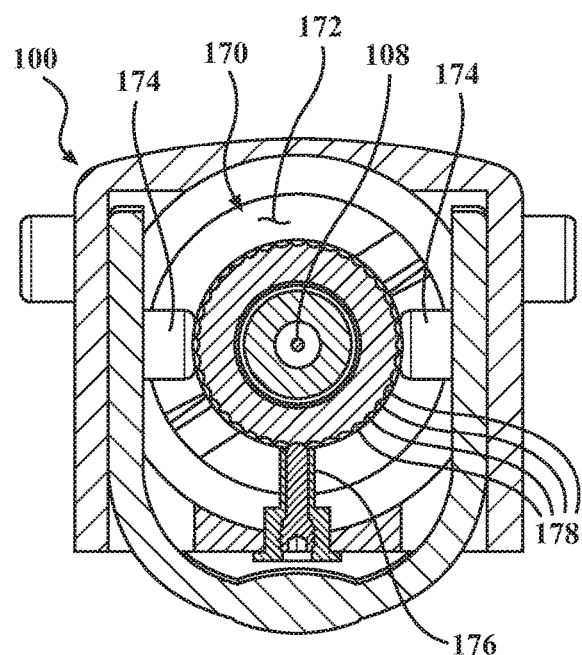
FIG. 15 is a cross-sectional view of the universal wire coupler of FIG. 2, illustrating the universal wire coupler comprising an adjustment mechanism positioned for accommodating a first surgical wire having a first diameter.
Figure 16:
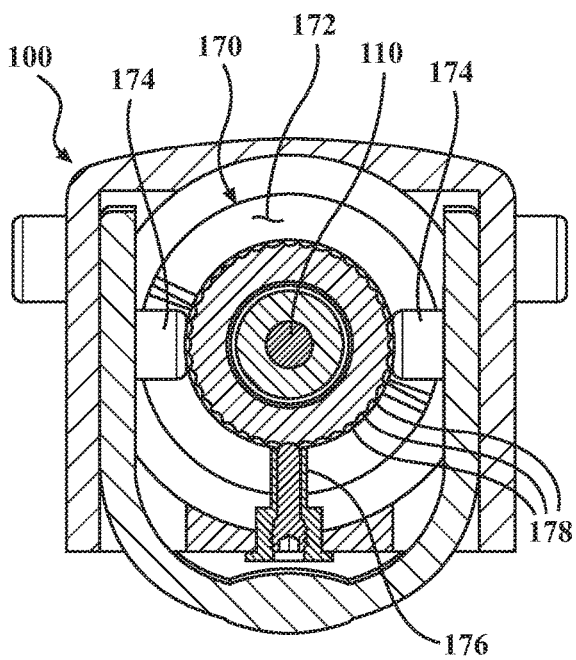
FIG. 16 is a cross-sectional view of the universal wire coupler of FIG. 2, illustrating the universal wire coupler comprising an adjustment mechanism positioned for accommodating a second surgical wire having a second diameter.
Figure 17:
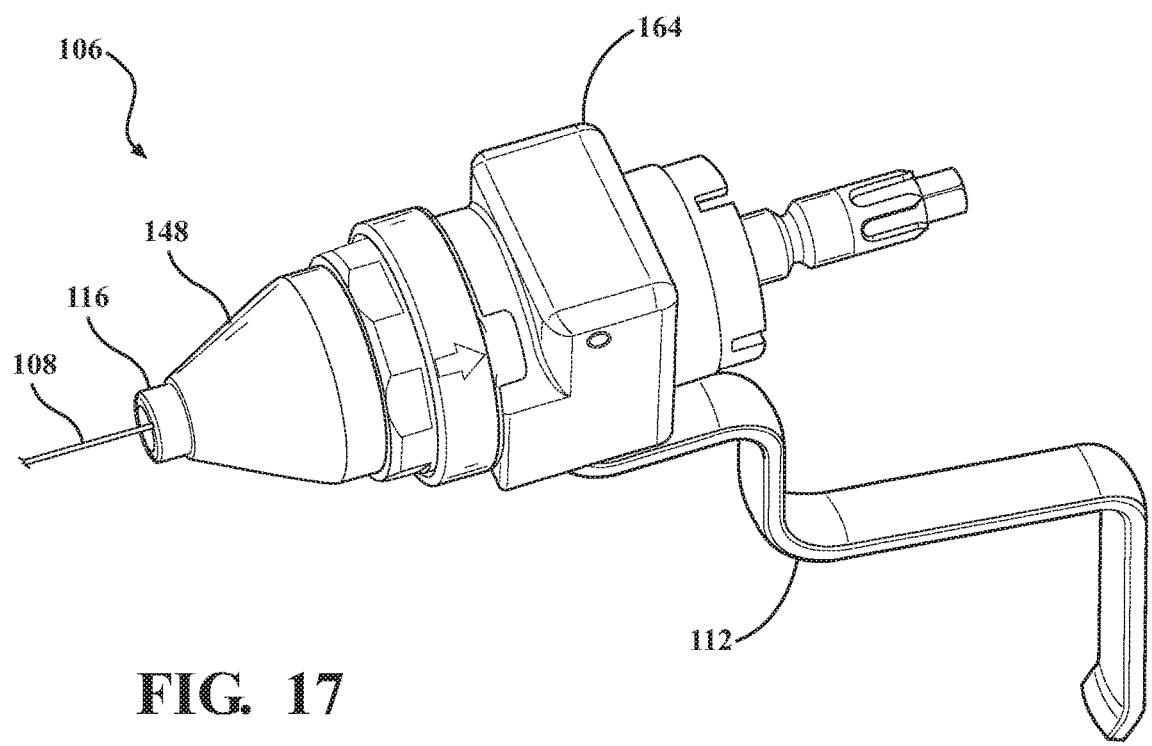
FIG. 17 is a perspective view of another universal wire coupler for use with surgical wires having a range of diameters.
Figure 18:
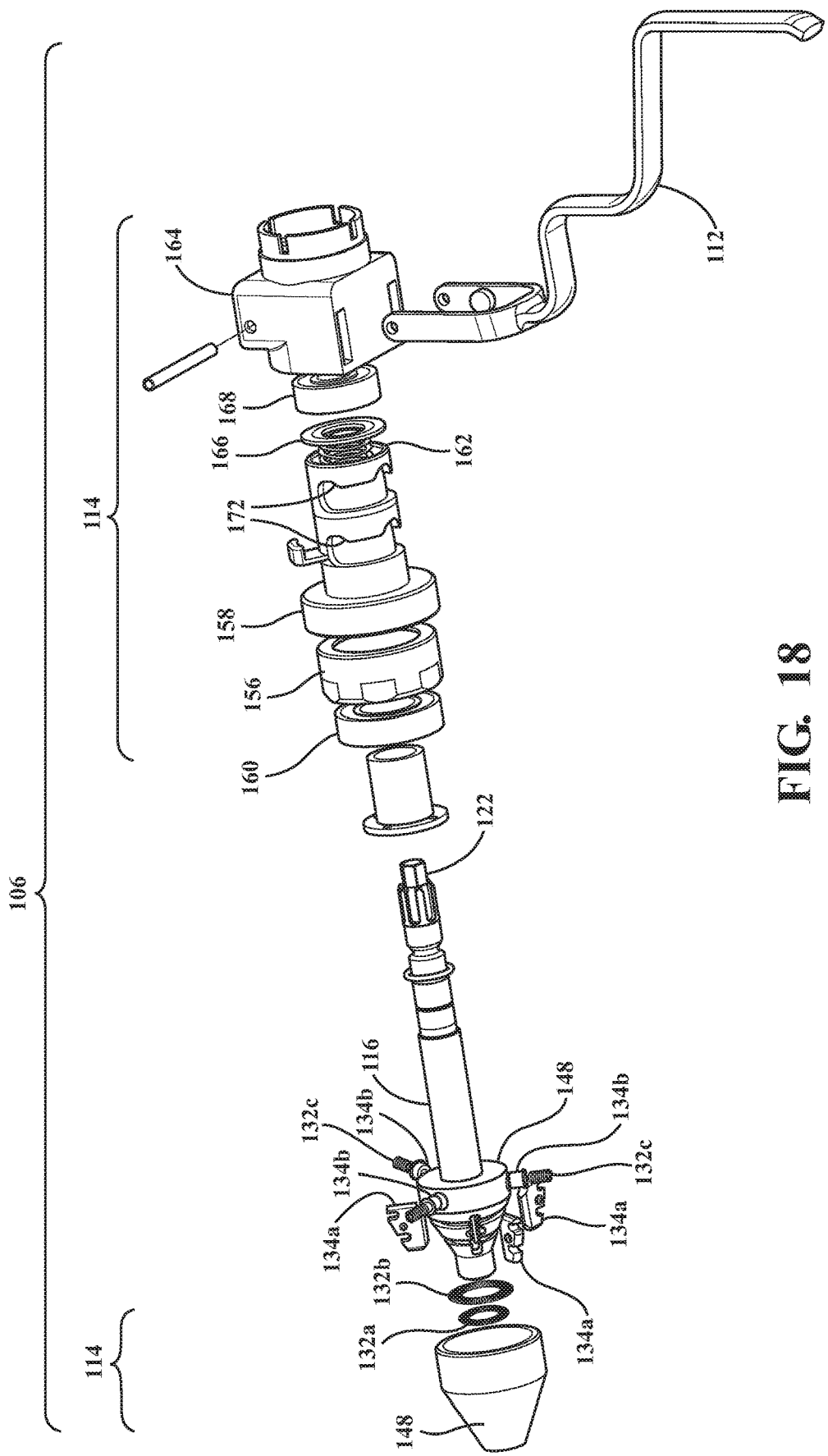
FIG. 18 is an exploded view of the universal wire coupler of FIG. 17, illustrating the universal wire coupler comprising two sets of jaws for securing surgical wires to the handheld surgical instrument.
Figure 19:
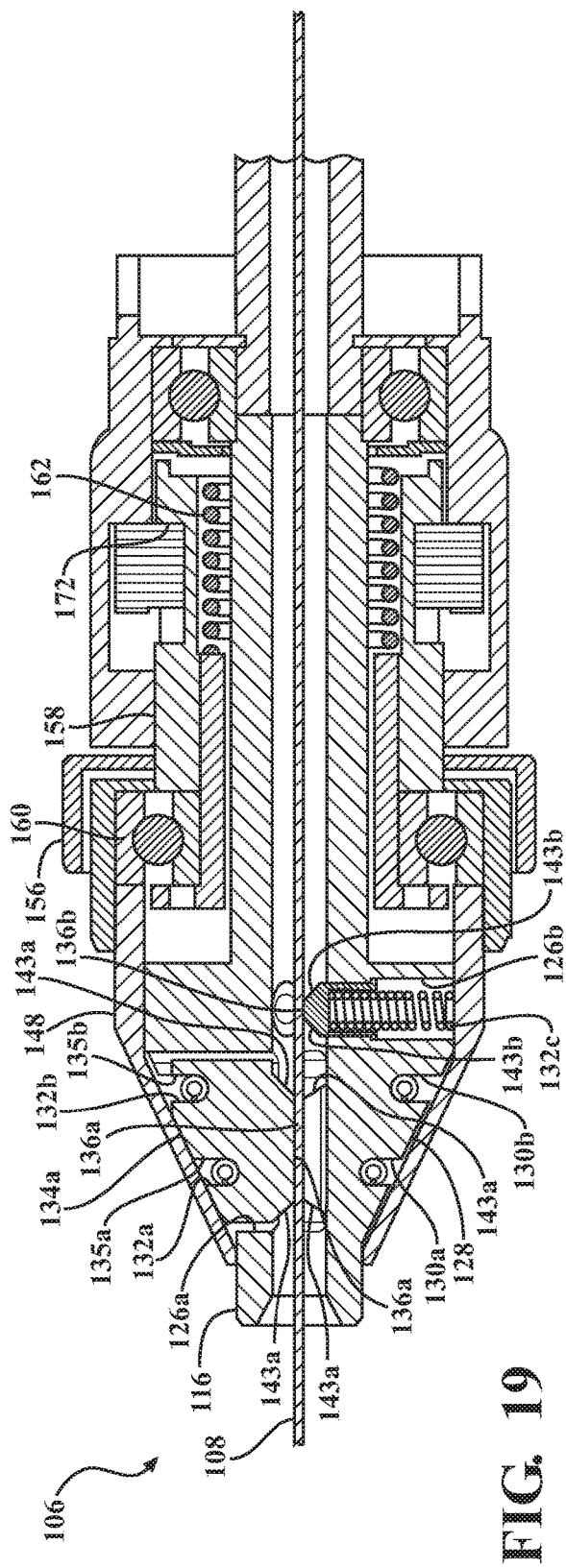
FIG. 19 is a cross-sectional view of the universal wire coupler of FIG. 17, illustrating the universal wire coupler comprising a securing mechanism disposed in a secured state for securing a first surgical wire having a first diameter within the jaws.
Figure 20:
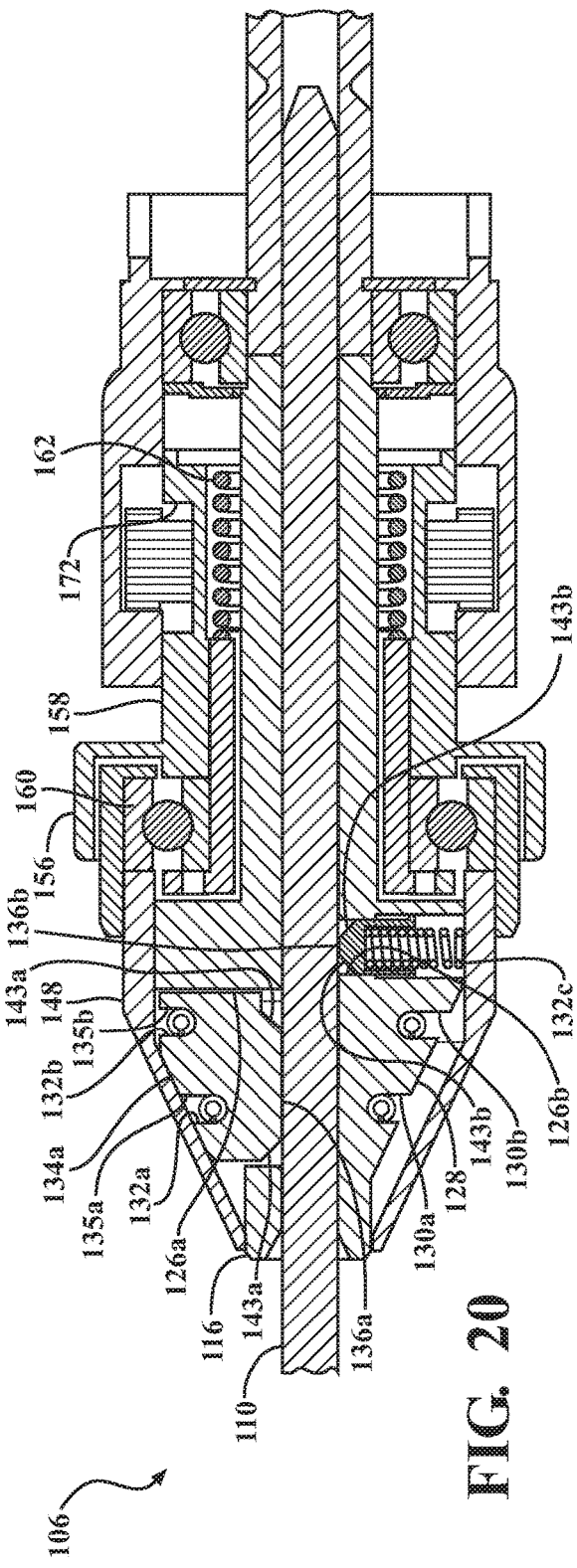
FIG. 20 is a cross-sectional view of the universal wire coupler of FIG. 19, illustrating the securing mechanism disposed in a secured state for securing a second surgical wire having a second diameter within the jaws.
Figure 30:
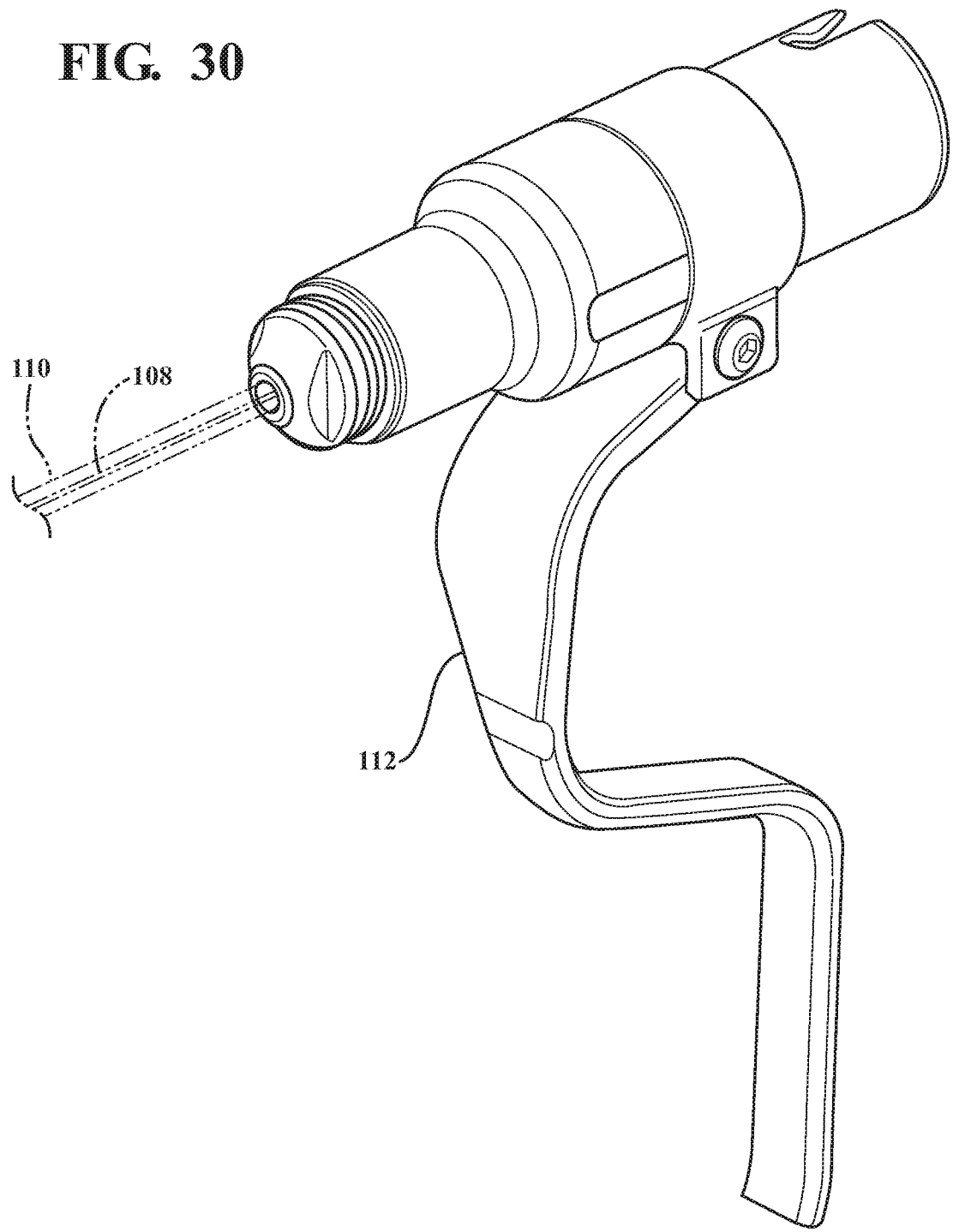
FIG. 30 is a perspective view of another universal wire coupler for use with surgical wires having a range of diameters.
Figure 31:
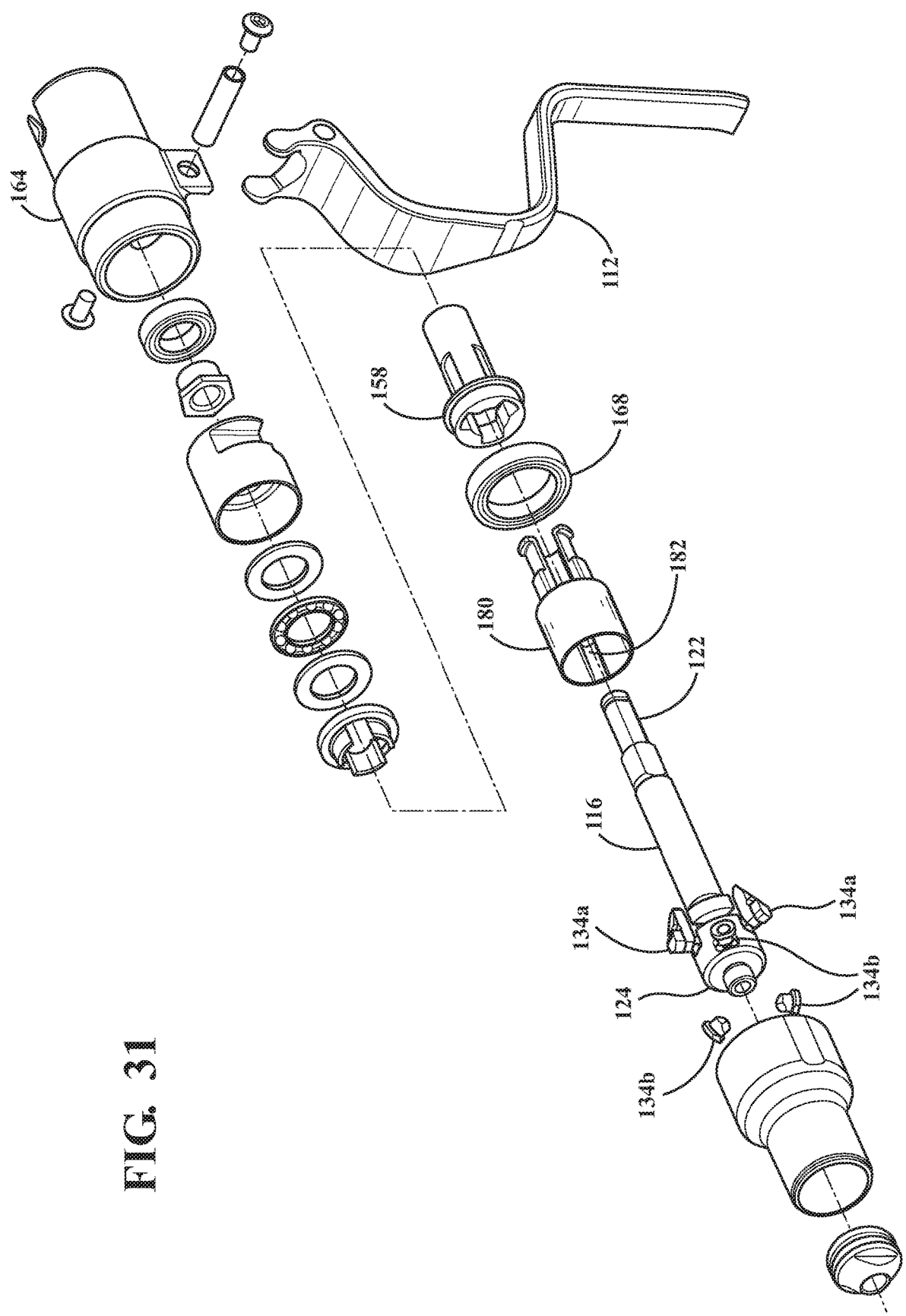
FIG. 31 is an exploded view of the universal wire coupler of FIG. 30, illustrating the universal wire coupler comprising a securing mechanism capable of moving in a distal direction towards a plurality of primary jaws to urge the primary jaws toward a longitudinal axis and increase a grip force of the primary jaws on a surgical wire.
Figure 32A:
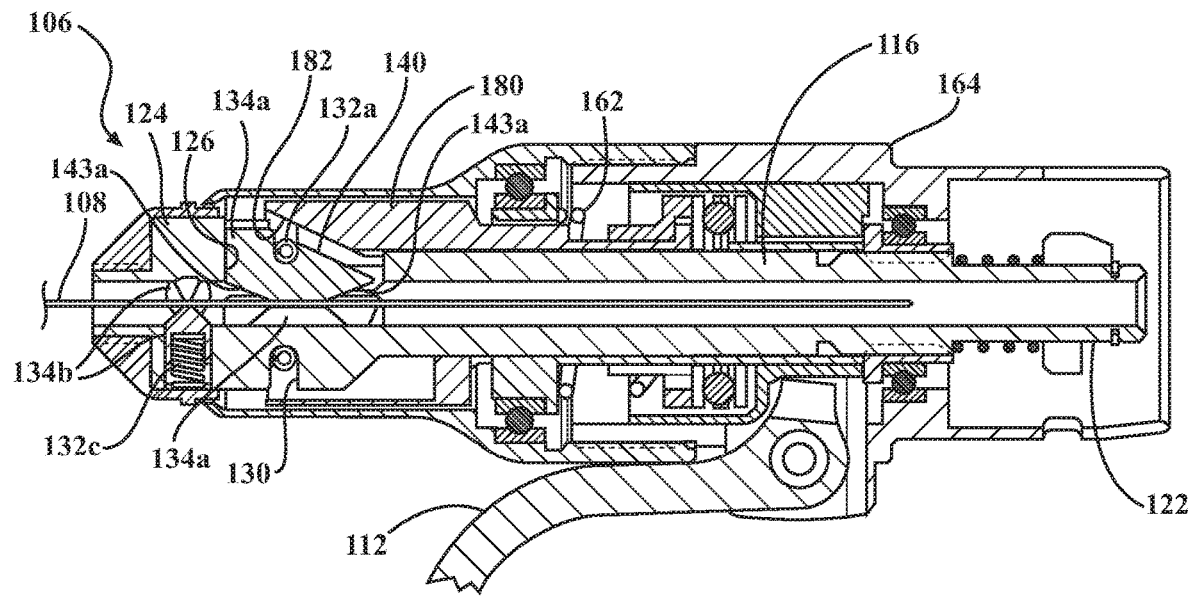
FIG. 32A is a cross-sectional view of the universal wire coupler of FIG. 30, illustrating the universal wire coupler comprising a securing mechanism disposed in an unsecured state to permit the primary jaws to move outward from a longitudinal axis when a first surgical wire having a first diameter is inserted between the primary jaws.
Figure 32B:
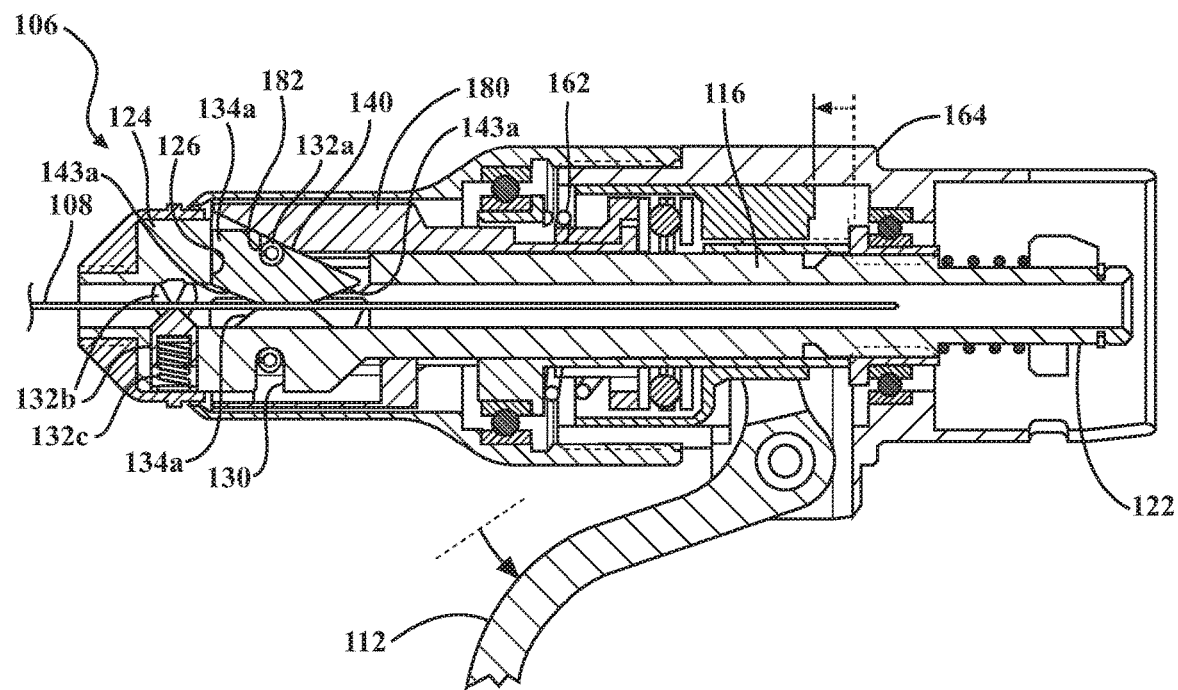
FIG. 32B is a cross-sectional view of the universal wire coupler of FIG. 32A, illustrating the securing mechanism in a secured state for increasing a grip force on the first surgical wire and securing the first surgical wire between the jaws.
Figure 33A:
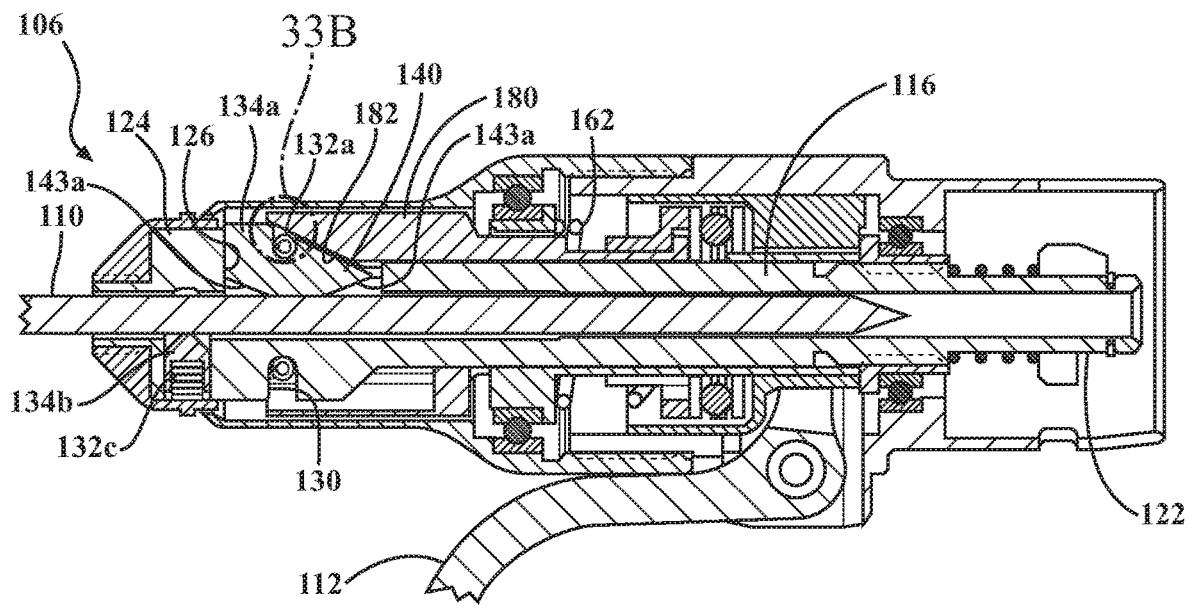
FIG. 33A is a cross-sectional view of the universal wire coupler of FIG. 32A, illustrating the securing mechanism disposed in an unsecured state to permit the primary jaws to move outward from the longitudinal axis when a second surgical wire having a second diameter is inserted between the primary jaws.
Figure 33B:
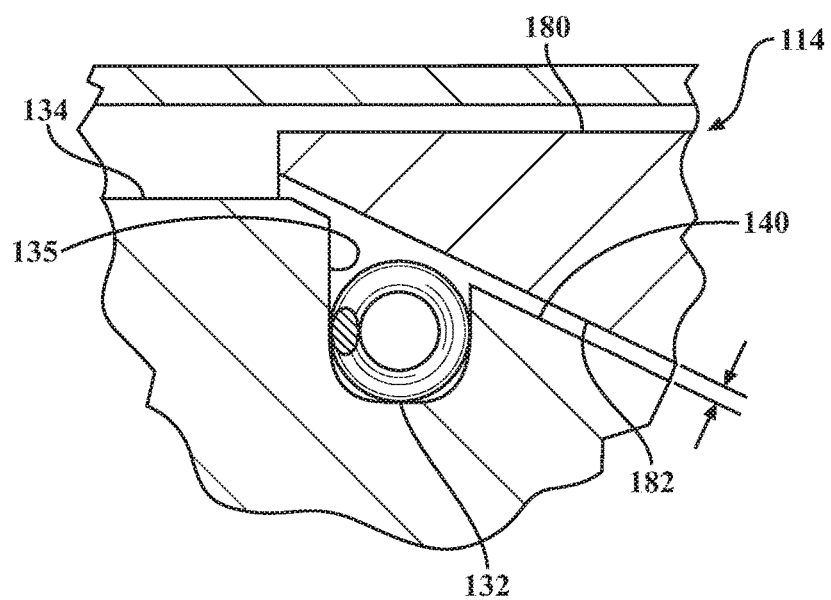
FIG. 33B is an enlarged view of the universal wire coupler of FIG. 33A, illustrating the securing mechanism in the unsecured state being spaced apart from the primary jaws.
Figure 33C:
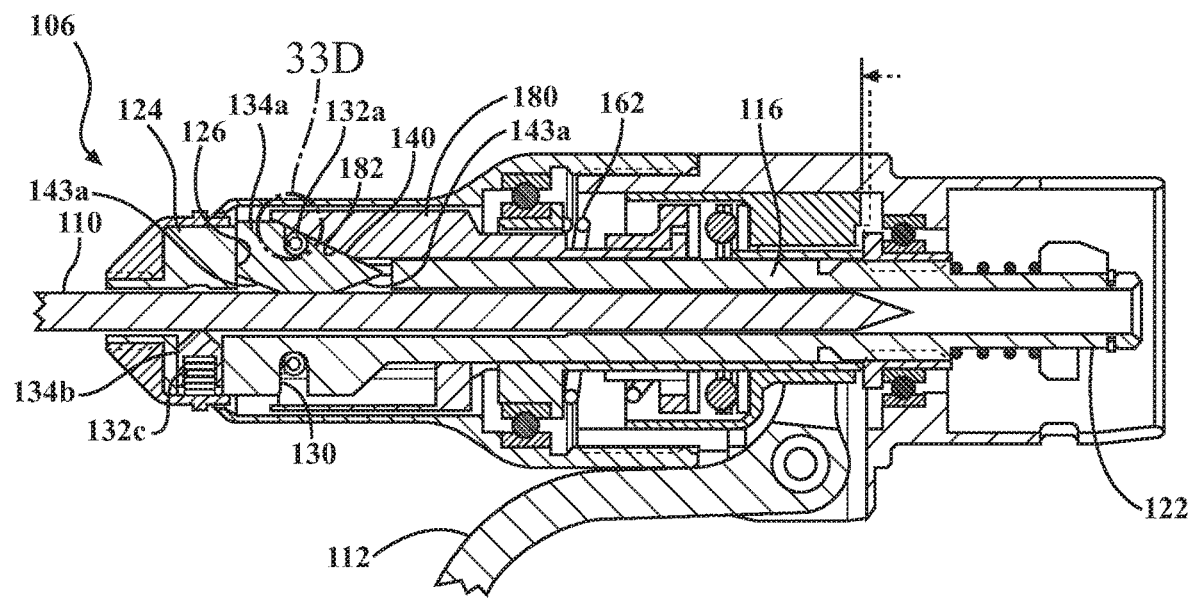
FIG. 33C is a cross-sectional view of the universal wire coupler of FIG. 32A, illustrating the securing mechanism in a secured state for increasing a grip force on the first surgical wire and securing the second surgical wire between the jaws.
Figure 33D:
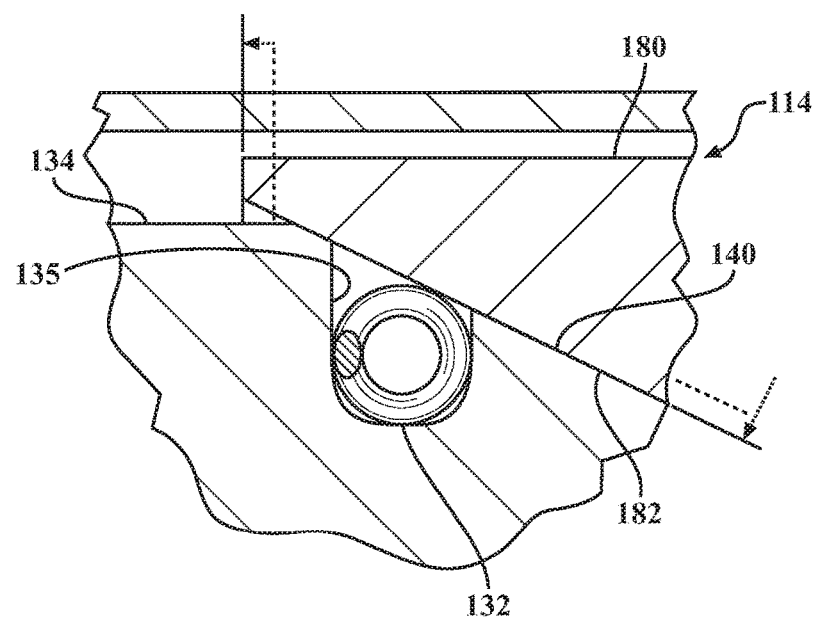
FIG. 33D is an enlarged view of the universal wire coupler of FIG. 33A, illustrating the securing mechanism in the secured state abutting against the primary jaws.

Referring to FIGS. 15 and 16, the universal wire coupler 106 may further comprise an adjustment mechanism 170 to adjust the axial position of the thruster 158 relative to the input device 112. The adjustment mechanism 170 may be engaged with the housing 164 and can be operated to calibrate the securing mechanism such that a reduced force on the input device 112 can secure larger or smaller surgical wires 108, 110 to the handheld surgical instrument 100 when the securing mechanism is in the secured state. In particular, the thruster 158 forms a cam surface 172, and the input device 112 comprises a pair of abutments 174 engaging the cam surface 172 to apply the axial force to the thruster 158 and move the securing mechanism 114 to the secured state when the input device is moved to the actuated state. The adjustment mechanism 170 may further comprise a detent 176, and the thruster 158 can comprise a plurality of ridges 178 capable of receiving the detent 176 and holding the cam surface 172 in a fixed position relative to the abutments 174. The detent 176 is removable from the ridges 178 to permit the thruster 158 to be rotated such that the cam surface 172 rotates relative to the abutments 174 of the input device 112 and the axial position of the securing mechanism 114 can be adjusted for one position of the input device 112. The adjustment mechanism 170 also improves the ergonomics of the universal wire coupler 106 in that the user with small hands does not have to reach as far forward to grip the input device 112 when gripping and driving surgical wires.

Referring now to FIGS. 17 through 29, an alternative universal wire coupler 106 similar to the universal wire coupler 106 of FIGS. 2 through 5 and comprises similar components identified by the same numbers.

However, as shown in FIGS. 21 and 22, each of the primary jaws 134a comprises a mounting member 137, illustrated as a pin. In addition, as shown in FIGS. 23 through 25, the universal wire coupler 106 further comprises the driveshaft 116 forming a plurality of guide slots 139 disposed perpendicularly from the longitudinal axis 120. The mounting members 137 are movably disposed along an associated one of the guide slots 139 such that the primary jaws 134 are capable of moving outward from the longitudinal axis 120 or inward towards the longitudinal axis 120 while the primary jaws 134 are constrained from moving in an axial direction along the longitudinal axis 120 during transition of the securing mechanism from the unsecured state to the secured state. The mounting members 137 and guide slots 139 are complementarily shaped such that the jaws can only move at an angle α described above for the coupler of FIGS. 2 through 16. The appropriate selection of α may reduce or prevent unintentional binding of the primary jaws 134 in the channels 126 after release of the input device 112. The appropriate selection of α may also reduce or prevent the primary jaws 134 from protruding from the handheld surgical instrument 100 in a manner that can tear a user's gloves or contact the patient. It is contemplated that movement of the jaws and the associated structure of the jaws and driveshaft can provide other benefits. Alternatively, it is contemplated that the driveshaft may form channels that are not spaced apart from the distal end but rather terminate at and communicate with the distal end such that jaws are capable of gripping surgical wires that broke during insertion and provide a gripping length or tip that cannot be inserted into the coupler substantially farther than the distal end.

The mounting members 137 and the guide slots 139 are further capable of constraining inward movement of the primary jaws 134a up to the longitudinal axis 120 such that the primary jaws 134a remain spaced outwardly from the longitudinal axis 120 when the securing mechanism 114 is in the secured state and the unsecured state. FIG. 21 illustrates the wire gripping surfaces 136a of the primary jaws 134a being spaced apart from one another when the mounting members 137 are seated at the end (FIG. 25) of the associated guide slots 139.

Referring to FIGS. 18 and 26 through 29, the universal wire coupler 106 further comprises a second plurality of jaws 134b configured to hold the surgical wire 108, 110 on the longitudinal axis 120 and facilitate insertion of surgical wires 108, 110 between the primary jaws 134a. More specifically, the universal wire coupler 106 may further comprise the driveshaft 116 forming a second plurality of channels 126b (FIG. 24) extending perpendicularly from the longitudinal axis 120. The second plurality of jaws 134b are movably disposed at least partially within an associated one of the second plurality of channels 126b. The second plurality of jaws 134b may comprise a second plurality of wire gripping surfaces 136 facing the longitudinal axis 120 and configured to grip the surgical wire 108, 110, inserted therebetween. The driveshaft 116 may comprise a distal end 144 adjacent to the distal region 124 carrying the primary jaws 134a. The primary jaws 134a may be positioned between the distal end 144 of the driveshaft 116 and the second plurality of jaws 134b, such that insertion of the surgical wires (FIGS. 19 and 20) into the handheld surgical instrument 100 in a distal direction permits the second plurality of jaws 134b to center the surgical wire 108, 110, within the lumen 118 and facilitate insertion between the primary jaws 134a.

As shown in FIGS. 26 and 28, each one of the second plurality of jaws 134b comprises a non-spherical shape configured to grip surgical wires 108, 110 having any diameter up to the diameter of the lumen 118, without permitting any one of second plurality of jaws 134b to become disposed entirely within the lumen 118. Each one of the second plurality of jaws 134b may comprise a cylinder terminating at a tip forming a convex surface, such that the second plurality of jaws 134b do not collide with one another when the jaws 134b are urged towards the longitudinal axis 120 for gripping the surgical wire 108.

Furthermore, the universal wire coupler 106 may further comprise a biasing member 132 engaged with at least one of the first plurality of jaws or the second plurality of jaws to urge the first plurality of jaws or the second plurality of jaws towards the lumen. While the universal wire coupler 106 of FIGS. 3 through 5 comprises only one the biasing member 132, the universal wire coupler 106 of FIGS. 18 through 20 comprises two biasing members 132a, 132b in the form of two garter springs that surround the primary jaws 134a and hold the primary jaws 134a within the channels 126a of the driveshaft 116. At least one of the primary jaws 134a comprises an inclined surface 140 positioned at an angle relative to the longitudinal axis 120 of the driveshaft 116. The inclined surface 140 of each primary jaw 134a forms two notches 135a, 135b aligned with associated grooves 130a, 130b formed in the outer surface 128 of the driveshaft 116. The notches 135a, 135b and grooves 130a, 130b may accommodate an associated one of the biasing members 132a, 132b. Each one of the second plurality of jaws 134b comprises an associated compression spring 132c for urging the corresponding jaw 134b toward the longitudinal axis 120 and applying a pre-grip force to the surgical wire 108, 110.

Referring to FIGS. 26 through 29, the primary and secondary jaws 134a, 134b are positioned relative to one another for centering the surgical wire 108, 110 in the lumen 118. The primary jaws 134a may be angularly spaced from one another by a first angle β, and the secondary jaws 134b may be angularly spaced from one another by a second angle θ. As best shown in FIGS. 26 and 28, the secondary jaws 134b may be positioned relative to the primary jaws 134a, such that each secondary jaw 134b is angularly centered between adjacent primary jaws 134a. It is contemplated that the primary and secondary jaws can be arranged in other suitable configurations for holding the surgical wire in any suitable position.

Referring now to FIGS. 30 through 33D, another alternative universal wire coupler 106 similar to the universal wire coupler 106 of FIGS. 2 through 5D comprises similar components identified by the same numbers. However, while the universal wire coupler 106 of FIGS. 2 through 5D comprises the securing mechanism 114 capable of moving in the proximal direction to the secured state, the universal wire coupler 106 comprises the securing mechanism 114 capable of moving in the opposite distal direction to the secured state towards the primary jaws 134. In particular, the securing mechanism 114 comprises a wedge 180 configured to urge the primary jaws 134 towards the lumen 118 of the driveshaft 116 when the securing mechanism 114 is transitioned from the unsecured state to the secured state. The wedge 180 is operatively coupled to the input device 112. The wedge 180 comprises an engagement surface 182 positioned relative to the longitudinal axis 120 at the angle corresponding with the inclined surfaces 140 of the primary jaws 134. The wedge 180 is disposed between the primary jaws 134 and the proximal region 122 of the driveshaft 116 such that the wedge 180 is movable distally toward the primary jaws 134 for disposing the securing mechanism 114 in the secured state and moving the primary jaws 134 inward toward the longitudinal axis 120.

Several wire couplers have been discussed in the foregoing description. However, the descriptions of the wire couplers discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described. It will be further appreciated that the terms "include," "includes," and "including" have the same meaning as the terms "comprise," "comprises," and "comprising."

What is claimed is:

1. A universal wire driver attachment for coupling a surgical wire having one of a range of diameters with a handheld surgical instrument, the universal wire driver attachment comprising:
   a driveshaft forming a lumen extending along a longitudinal axis, the driveshaft having a proximal region and a distal region forming a plurality of channels extending perpendicularly from the longitudinal axis, the distal region of the driveshaft comprising a plurality of channel surfaces surrounding an associated one of the plurality of channels to constrain a plurality of primary jaws from moving in an axial direction along the longitudinal axis, the driveshaft terminating at a distal end, and the plurality of primary jaws are spaced apart from the distal end towards the proximal region of the driveshaft;
   the plurality of primary jaws movably disposed at least partially within the associated one of the plurality of channels, the plurality of primary jaws comprising a plurality of wire gripping surfaces facing the longitudinal axis and configured to grip the surgical wire inserted therebetween, the plurality of primary jaws cooperate with the plurality of channels such that the plurality of primary jaws are constrained from moving in the axial direction along the longitudinal axis, and at least one of the plurality of primary jaws comprises an inclined surface positioned at an angle relative to the longitudinal axis of the driveshaft;
   a biasing member configured to urge the plurality of primary jaws inward toward the longitudinal axis to grip the surgical wire;
   an input device movably disposed between an actuated position and a non-actuated position; and
   a securing mechanism engaged with the input device, the securing mechanism movably disposed between a secured state when the input device is disposed in the actuated position and an unsecured state when the input device is disposed in the non-actuated position, and the securing mechanism is movably disposed along the longitudinal axis to engage the inclined surface and move the primary jaws inwardly toward the longitudinal axis, and the securing mechanism comprises an engagement surface positioned relative to the longitudinal axis at the angle corresponding with the inclined surface to urge the plurality of primary jaws towards the lumen of the driveshaft when the securing mechanism is transitioned from the unsecured state to the secured state;
   wherein the plurality of primary jaws are capable of moving outward from the longitudinal axis when the surgical wire is inserted between the plurality of primary jaws and the plurality of primary jaws are capable of being urged inward toward the longitudinal axis by the securing mechanism to increase a grip force on the surgical wire when the securing mechanism is in the secured state.

2. The universal wire driver attachment of claim 1, wherein the driveshaft comprises an outer surface facing the securing mechanism, and each one of the plurality of primary jaws comprises a flange configured to engage the outer surface of the driveshaft and prevent the associated primary jaw from moving in an inward direction past the longitudinal axis of the driveshaft.

3. The universal wire driver attachment of claim 1, wherein the plurality of wire gripping surfaces of the plurality of primary jaws remain disposed in the lumen of the driveshaft when the securing mechanism is disposed in the secured state or the unsecured state.

4. The universal wire driver attachment of claim 1, wherein the biasing member is a spring.

5. The universal wire driver attachment of claim 4 wherein the spring is a garter spring surrounding the plurality of primary jaws and holding the plurality of primary jaws within the plurality of channels of the driveshaft.

6. The universal wire driver attachment of claim 1, wherein at least one of the plurality of primary jaws comprises the inclined surface positioned at the angle relative to the longitudinal axis of the driveshaft, and the inclined surface forms a notch configured to receive the biasing member.

7. The universal wire driver attachment of claim 6 wherein the driveshaft comprises an outer surface facing the securing mechanism and forming a groove aligned with the notch of the primary jaws, and the biasing member is received within the notch and the groove such that the notch and the groove provide clearance for the securing mechanism.

8. The universal wire driver attachment of claim 1 wherein the securing mechanism comprises a wedge operatively coupled to the input device and the wedge comprises the engagement surface.

9. The universal wire driver attachment of claim 8 wherein the driveshaft comprises the distal end adjacent to the distal region, and the wedge is disposed between the plurality of primary jaws and the proximal region such that the wedge is movable forward toward the plurality of primary jaws for disposing the securing mechanism in the secured state and moving the plurality of primary jaws inward toward the longitudinal axis.

10. The universal wire driver attachment of claim 1, wherein the securing mechanism comprises a nose cone operatively coupled to the input device, and the nose cone comprises the engagement surface.

11. The universal wire driver attachment of claim 10, wherein the securing mechanism further comprises:
a hood linearly secured to the nose cone such that the hood and the nose cone are linearly movable in unison along the longitudinal axis and the hood is capable of transmitting a thrust load to the nose cone for urging the plurality of primary jaws towards the lumen; and
a thruster capable of transmitting the thrust load from the input device to the hood when the securing mechanism is in the secured state and the input device is moved to the actuated position.

12. The universal wire driver attachment of claim 11 wherein the hood is rotatably coupled to the nose cone to permit the nose cone to freely rotate relative to the hood.

13. The universal wire driver attachment of claim 11, further comprising a bearing configured to transmit the thrust load from the hood to the nose cone while permitting the nose cone to rotate relative to the hood.

14. The universal wire driver attachment of claim 10, wherein the driveshaft comprises the distal end adjacent the distal region carrying the plurality of primary jaws, and the nose cone is disposed forward of the distal end such that the nose cone is movable rearward toward the plurality of primary jaws for disposing the securing mechanism in the secured state and moving the plurality of primary jaws inward toward the longitudinal axis.

15. The universal wire driver attachment of claim 10, wherein the nose cone and the driveshaft are movably disposable relative to one another along the longitudinal axis such that the nose cone is linearly movable along the longitudinal axis relative to the driveshaft when the securing mechanism is moved between the secured state and the unsecured state.

16. The universal wire driver attachment of claim 10, wherein the nose cone and the driveshaft are rotatably secured to one another such that the driveshaft is capable of transmitting torque to the nose cone to rotate the driveshaft and the nose cone in unison about the longitudinal axis.

17. The universal wire driver attachment of claim 10, wherein one of the nose cone and the driveshaft comprises a protrusion and the other of the nose cone and the driveshaft comprises a nose cone slot extending parallel to the longitudinal axis and receiving the protrusion.

18. A handheld wire driver for driving a surgical wire, comprising:
a handpiece having a drive system; and
a universal wire coupler capable of transmitting torque from the drive system to the surgical wire, the universal wire coupler comprising:
a driveshaft forming a lumen extending along a longitudinal axis, the driveshaft having a proximal region and a distal region forming a plurality of channels extending perpendicularly from the longitudinal axis, the distal region of the driveshaft comprising a plurality of channel surfaces surrounding an associated one of the plurality of channels to constrain a plurality of primary jaws from moving in an axial direction along the longitudinal axis, the driveshaft terminating at a distal end, and the plurality of primary jaws are spaced apart from the distal end towards the proximal region of the driveshaft;
the plurality of primary jaws movably disposed at least partially within the associated one of the plurality of channels, the plurality of primary jaws comprising a plurality of wire gripping surfaces facing the longitudinal axis and configured to grip the surgical wire inserted therebetween, the plurality of primary jaws cooperate with the plurality of channels such that the plurality of primary jaws are constrained from moving in the axial direction along the longitudinal axis, and at least one of the plurality of primary jaws comprises an inclined surface positioned at an angle relative to the longitudinal axis of the driveshaft;
a biasing member configured to urge the plurality of primary jaws inward toward the longitudinal axis to grip the surgical wire;
an input device movably disposed between an actuated position and a non- actuated position; and
a securing mechanism engaged with the input device, the securing mechanism movably disposed between a secured state when the input device is disposed in the actuated position and an unsecured state when the input device is disposed in the non-actuated position, and the securing mechanism is movably disposed along the longitudinal axis to engage the inclined surface and move the primary jaws inwardly toward the longitudinal axis, and the securing mechanism comprises an engagement surface positioned relative to the longitudinal axis at the angle corresponding with the inclined surface to urge the plurality of primary jaws towards the lumen of the driveshaft when the securing mechanism is transitioned from the unsecured state to the secured state;

wherein the plurality of primary jaws are capable of moving outward from the longitudinal axis when the surgical wire is inserted between the plurality of primary jaws, and the plurality of primary jaws are capable of being urged inward toward the longitudinal axis by the securing mechanism to increase a grip force on the surgical wire when the securing mechanism is in the secured state.

19. The handheld wire driver of claim 18 wherein the universal wire coupler is an integral portion of the handpiece.

20. The handheld wire driver of claim 18 wherein the universal wire coupler is an attachment that is removably coupleable to the handpiece.

\* \* \* \* \*